(12) United States Patent
Takahira et al.

(10) Patent No.: US 10,358,400 B2
(45) Date of Patent: *Jul. 23, 2019

(54) METHOD FOR PRODUCING OLEFIN CONTAINING CHLORINE AND FLUORINE

(71) Applicant: AGC Inc., Chiyoda-ku (JP)

(72) Inventors: Yusuke Takahira, Tokyo (JP); Daisuke Jomuta, Tokyo (JP)

(73) Assignee: AGC Inc., Chiyoda-ku (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/633,435

(22) Filed: Jun. 26, 2017

(65) Prior Publication Data

US 2017/0291863 A1    Oct. 12, 2017

Related U.S. Application Data

(63) Continuation of application No. PCT/JP2015/085865, filed on Dec. 22, 2015.

(30) Foreign Application Priority Data

Dec. 26, 2014    (JP) .................. 2014-266097

(51) Int. Cl.
*C07C 6/04*    (2006.01)
*B01J 23/24*    (2006.01)
(Continued)

(52) U.S. Cl.
CPC .................. *C07C 6/04* (2013.01); *B01J 23/24* (2013.01); *B01J 23/28* (2013.01); *B01J 31/1805* (2013.01);
(Continued)

(58) Field of Classification Search
CPC ............. C07C 6/04; C07C 17/00; B01J 23/24
See application file for complete search history.

(56) References Cited

U.S. PATENT DOCUMENTS 9,598,335 B2 *  3/2017  Takahira ............. C07C 41/22
9,796,647 B2 *  10/2017  Takahira ............. C07C 41/30
(Continued)

FOREIGN PATENT DOCUMENTS

EP    2703081 A1 *  3/2014  .......... B01J 31/1608
WO    02/079126    10/2002
(Continued)

OTHER PUBLICATIONS

Copending U.S. Appl. No. 15/633,336 (Year: 2017).*
(Continued)

*Primary Examiner* — Rosalynd K Keys
(74) *Attorney, Agent, or Firm* — Oblon, McClelland, Maier & Neustadt, L.L.P.

(57) ABSTRACT

A method for producing at least one olefin compound selected from the group consisting of a compound of formula (51) and a compound of formula (52), the method including reacting an olefin compound of formula (21) with a olefin compound of formula (31) in the presence of at least one metal catalyst selected from the group consisting of a compound of formula (11), a compound of formula (12), a compound of formula (13), a compound of formula (14), and a compound of formula (15).

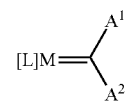

(11)

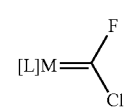

(12)

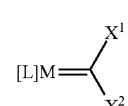

(13)

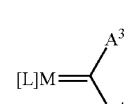

(14)

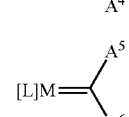

(15)

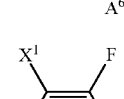

(21)

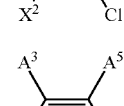

(31)

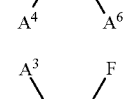

(51)

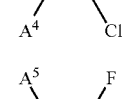

(52)

15 Claims, No Drawings

(51) Int. Cl.
    *C07C 21/04*      (2006.01)
    *C07C 21/18*      (2006.01)
    *C07C 67/287*     (2006.01)
    *C07C 67/307*     (2006.01)
    *C07C 41/22*      (2006.01)
    *C07D 207/27*     (2006.01)
    *C07D 209/86*     (2006.01)
    *C07C 17/361*     (2006.01)
    *B01J 23/28*      (2006.01)
    *B01J 31/18*      (2006.01)
    *B01J 31/22*      (2006.01)
    *C07B 61/00*      (2006.01)

(52) U.S. Cl.
    CPC ....... *B01J 31/2226* (2013.01); *B01J 31/2265* (2013.01); *C07C 17/361* (2013.01); *C07C 21/04* (2013.01); *C07C 21/18* (2013.01); *C07C 41/22* (2013.01); *C07C 67/287* (2013.01); *C07C 67/307* (2013.01); *C07D 207/27* (2013.01); *C07D 209/86* (2013.01); *B01J 2231/543* (2013.01); *B01J 2531/64* (2013.01); *C07B 61/00* (2013.01)

(56) References Cited

U.S. PATENT DOCUMENTS

| | | | |
|---|---|---|---|
| 2003/0100776 A1* | 5/2003 | Grubbs | C07C 6/04 549/513 |
| 2013/0190518 A1* | 7/2013 | Mauduit | C07C 29/32 554/121 |
| 2016/0176791 A1 | 6/2016 | Takahira | |
| 2017/0101360 A1 | 4/2017 | Takahira | |

FOREIGN PATENT DOCUMENTS

| | | |
|---|---|---|
| WO | 2009/003085 | 12/2008 |
| WO | 2015/033927 | 3/2015 |

OTHER PUBLICATIONS

Copending U.S. Appl. No. 15/706,164 (Year: 2017).*
Extended European Search Report dated Dec. 8, 2017 in Patent Application No. 15873091.1, citing documents AW-AY therein, 8 pages.
Michael J. Van Hamme, et al., "A Facile One-Step Preparation of Chlorofluoromethylene Olefins" Journal of Fluorine Chemistry, vol. 10, No. 2, XP055428323, Aug. 1977, pp. 131-143.
Hiroki Yamanaka, et al., "Preparation of 1-Choro-1-Fluoroethylenes Via Chlorofluorocarbene" Bulletin of the Chemical Society of Japan, vol. 41, No. 3, XP055428319, Mar. 1968, pp. 756-759.
Chen Chen, et al., "Synthesis of Fluorinated Olefins Via the Palladium Catalysed Cross-Coupling Reaction of 1-Fluorovinyl Halides with Organoboranes" Tetrahedron Letters, vol. 40, No. 5, XP004151457, Jan. 29, 1999. pp. 827-830.
International Search Report issued in PCT/JP2015/085865, filed Dec. 22, 2015.
Macnaughton, M.L. "Ruthenium-Catalyzed Metathesis with Directly Functionalized Olefins", (online), retrieval date Nov. 19, 2014. (2009).
Chatterjee, A.K., et al., "A General Model for Selectivity in Olefin Cross Metathesis", American Chemical Society, vol. 125 pp. 11360-11370. (2003).
Schrock, R.R., "What's New in Olefin Metathesis Catalyzed by Molybdenum and Tungsten Complexes", Chemistry in New Zealand, pp. 117-121. (Jul. 2011).
Schrock, R.R., et al., "Molybdenum and Tungsten Imido Alkylidene Complexes as Efficient Olefin-Metathesis Catalysts", Angewandte Chemie International Edition, vol. 42 pp. 4592-4633. (2003).
Takahira, Y., et al., "Ruthenium-Catalyzed Olefin Cross-Metathesis with Tetrafluoroethylene and Analogous Fluoroolefins", Journal of the American Chemical Society, vol. 137, pp. 7031-7034. (2015).
Trnka, T.M., et al., "Olefin Metathesis with 1,1-Difluoroethylene", Angewandte Chemie International Edition, vol. 40, No. 18, pp. 3441-3444. (2001).
Written Opinion Issued in PCT/JP2015/085865, filed Dec. 22, 2015.

* cited by examiner

METHOD FOR PRODUCING OLEFIN CONTAINING CHLORINE AND FLUORINE

TECHNICAL FIELD

The present invention relates to a novel method for producing an olefin containing chlorine and fluorine through olefin metathesis.

BACKGROUND ART

Among olefin compounds where a part or all of hydrogen atoms are substituted with a chlorine atom and a fluorine atom, that is, olefins containing chlorine and fluorine, some industrially-useful compounds are known, however, no method for simply and efficiently producing these compounds has been established yet. For example, Patent Document 1 discloses a method in which an olefin is reacted with fluorine gas in the presence of anhydrous hydrogen fluoride, however, this reaction is extremely exothermic and, hence, must be performed at an extremely low temperature, e.g., −70° C. In addition, by-products are produced in a large amount.

Consequently, if other olefins containing chlorine and fluorine could be simply and efficiently produced from industrially-easily-available fluorine-containing olefins such as R-1112, i.e., 1,2-dichloro-1,2-difluoroethylene, and R-1131a, i.e., 1-chloro-1-fluoroethylene under mild conditions, the method could be an extremely useful synthesis method as compared with already-existing methods.

On the other hand, olefin metathesis reaction that is a double bond recombination reaction with a metal catalyst (hereinafter this may be simply referred to as "olefin metathesis") is widely utilized as a production method for olefins having various types of substituents. However, electron-deficient olefins having an electron-withdrawing substituent have low reactivity, and therefore use thereof in olefin metathesis is not easy. For example, Non-Patent Document 1 investigates the reactivity of olefins having various substituents and describes that the reactivity of electron-deficient olefins is low. In fact, olefins having a halogen such as a fluorine atom or a chlorine atom are electron-deficient olefins, and therefore there are few reports using them in olefin metathesis. For example, in Non-Patent Document 2, olefin metathesis of a ruthenium complex and vinylidene fluoride (i.e., 1,1-difluoroethylene) is investigated, but the report describes that the expected products, that is, ethylene and tetrafluoroethylene could not be obtained at all.

PRIOR ART DOCUMENTS

Patent Document

Patent Document 1: International Publication WO 2012/007310

Non-Patent Documents

Non-Patent Document 1: Chatterjee, A. K. et al., *J. Am. Chem. Soc.*, 2003, 125, 11360-11370.
Non-Patent Document 2: Trnka, T. et al., *Angew. Chem. Int. Ed.*, 2001, 40, 3441-3444

SUMMARY OF THE INVENTION

Problems that the Invention is to Solve

In that manner, use of halogen atom-containing olefins in olefin metathesis is not practicable. Above all, tetrafluoroethylene and hexafluoropropylene are useful compounds from the viewpoint of industrial easy availability and commercialization, however, these are not only extremely electron-deficient olefins but also difficult to handle, and therefore there has been no report relating to use thereof in olefin metathesis.

Accordingly, an object of the present invention is to provide a method for producing other olefins containing chlorine and fluorine in a simplified manner and efficiently from industrially-easily-available olefins containing chlorine and fluorine such as R-1112, i.e., 1,2-dichloro-1,2-difluoroethylene, and R-1131a, i.e., 1-chloro-1-fluoroethylene under mild conditions through olefin metathesis.

Means for Solving the Problem

As a result of assiduous studies, the present inventors have found that an olefin containing chlorine and fluorine, such as R-1112, i.e., 1,2-dichloro-1,2-difluoroethylene, or R-1131a, i.e., 1-chloro-1-fluoroethylene, and an olefin substituted with an organic group give another olefin containing chlorine and fluorine under mild conditions in the presence of a metal catalyst having a metal-carbon double bond. The present invention has been thus completed.

The present invention relates to the following [1] to [13].

[1]
A method for producing at least one kind of an olefin compound selected from the group consisting of a compound represented by the following formula (51) and a compound represented by the following formula (52), the method including performing a reaction of a olefin compound represented by the following formula (21) with a olefin compound represented by the following formula (31) in the presence of at least one kind of a metal catalyst selected from the group consisting of a compound represented by the following formula (11), a compound represented by the following formula (12), a compound represented by the following formula (13), a compound represented by the following formula (14), and a compound represented by the following formula (15).

[Chem. 1]

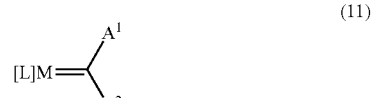

(11)

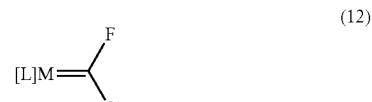

(12)

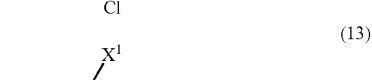

(13)

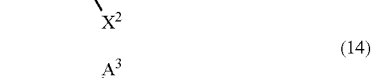

(14)

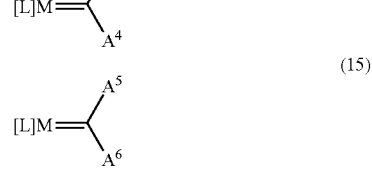

(15)

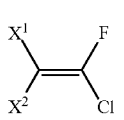
(21)

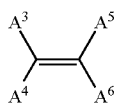
(31)

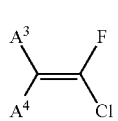
(51)

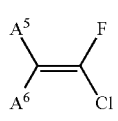
(52)

In the formulae, the symbols represent the following meanings.

[L] is a ligand. M is ruthenium, molybdenum or tungsten.

$A^1$ to $A^6$ are each independently a functional group selected from the group consisting of the following functional group (i), functional group (ii), functional group (iii), and functional group (iv). $A^1$ and $A^2$ may bond to each other to form a ring. $A^3$ and $A^4$ may bond to each other to form a ring. $A^5$ and $A^6$ may bond to each other to form a ring. In the case where one of $A^1$ or $A^2$ is a halogen atom, the other is a functional group selected from the group consisting of the functional group (i), the functional group (iii) and the functional group (iv). In the case where one of $A^3$ or $A^4$ is a halogen atom, the other is a functional group selected from the group consisting of the functional group (i), the functional group (iii) and the functional group (iv). In the case where one of the $A^5$ or $A^6$ is a halogen atom, the other is a functional group selected from the group consisting of the functional group (i), the functional group (iii) and the functional group (iv).

$X^1$ and $X^2$ are each independently a functional group selected from the group consisting of the following functional group (i), functional group (ii), functional group (v), and functional group (vi), and they may bond to each other to form a ring. In the case where one of $X^1$ or $X^2$ is a fluorine atom, the other is a functional group selected from the group consisting of the functional group (i), a halogen atom except for a fluorine atom, the functional group (v) and the functional group (vi).

Functional group (i): a hydrogen atom.

Functional group (ii): a halogen atom.

Functional group (iii): a monovalent hydrocarbon group having a carbon number of from 1 to 20.

Functional group (iv): a monovalent hydrocarbon group having a carbon number of from 1 to 20 and containing one or more atoms selected from the group consisting of a halogen atom, an oxygen atom, a nitrogen atom, a sulfur atom, a phosphorus atom, and a silicon atom.

Functional group (v): a functional group selected from the group consisting of an alkyl group having a carbon number of from 1 to 12, an alkoxy group having a carbon number of from 1 to 12, an aryl group having a carbon number of from 5 to 20, an aryloxy group having a carbon number of from 5 to 20, a (per)halogenated alkyl group having a carbon number of from 1 to 12, a (per)halogenated alkoxy group having a carbon number of from 1 to 12, a (per)halogenated aryl group having a carbon number of from 5 to 20, and a (per)halogenated aryloxy group having a carbon number of from 5 to 20.

Functional group (vi): the functional group (v) containing one or more atoms selected from the group consisting of an oxygen atom, a nitrogen atom, a sulfur atom, a phosphorus atom, and a silicon atom.

[2]

The production method according to the above [1], satisfying a combination where in the olefin compound represented by the formula (21), $X^1$ is the functional group (i), the functional group (ii), the functional group (v), or the functional group (vii) and $X^2$ is the functional group (ii), the functional group (v), or the functional group (vii).

Here, the functional group (i), the functional group (ii), and the functional group (v) have the same meanings as those in claim 1, and the functional group (vii) is the functional group (v) having an etheric oxygen atom between a carbon atom and a carbon atom.

[3]

The production method according to the above [1], including performing a reaction of at least any one compound selected from the group consisting of 1-chloro-1-fluoroethylene, 1,2-dichloro-1,2-difluoroethylene, and 1,3,3-trichloro-1,2,3-trifluoropropene as the olefin compound represented by the formula (21).

[4]

The production method according to any one of the above [1] to [3], wherein a metal of the metal catalyst is ruthenium.

[5]

The production method according to any one of the above [1] to [3], wherein a metal of the metal catalyst is molybdenum or tungsten, and the metal catalyst has an imide ligand and a ligand including two coordinating oxygen atoms as the ligand [L].

[6]

The production method according to any one of the above [1] to [5], wherein the olefin compound represented by the formula (31) is ethylene, a monosubstituted olefin, or a 1,2-disubstituted olefin.

[7]

The production method according to any one of the above [1] to [6], wherein in the olefin compound represented by the formula (31), $A^3$ is a hydrogen atom and $A^4$ is a hydrogen atom, a monovalent hydrocarbon group having a carbon number of from 1 to 20, or a monovalent hydrocarbon group having a carbon number of from 1 to 20 and containing one or more atoms selected from the group consisting of a halogen atom, an oxygen atom, a nitrogen atom, a sulfur atom, a phosphorus atom, and a silicon atom.

[8]

The production method according to any one of the above [1] to [7], wherein the olefin compound represented by the formula (31) is at least one kind of an olefin compound selected from olefin compounds represented by the following formulae.

In the following formulae, R is an alkyl group having a carbon number of from 1 to 12 or an alkyl group having a carbon number of from 1 to 12 and having an etheric oxygen atom between a carbon atom and a carbon atom, and Ar is an aryl group having a carbon number of from 5 to 12.

[Chem. 2]

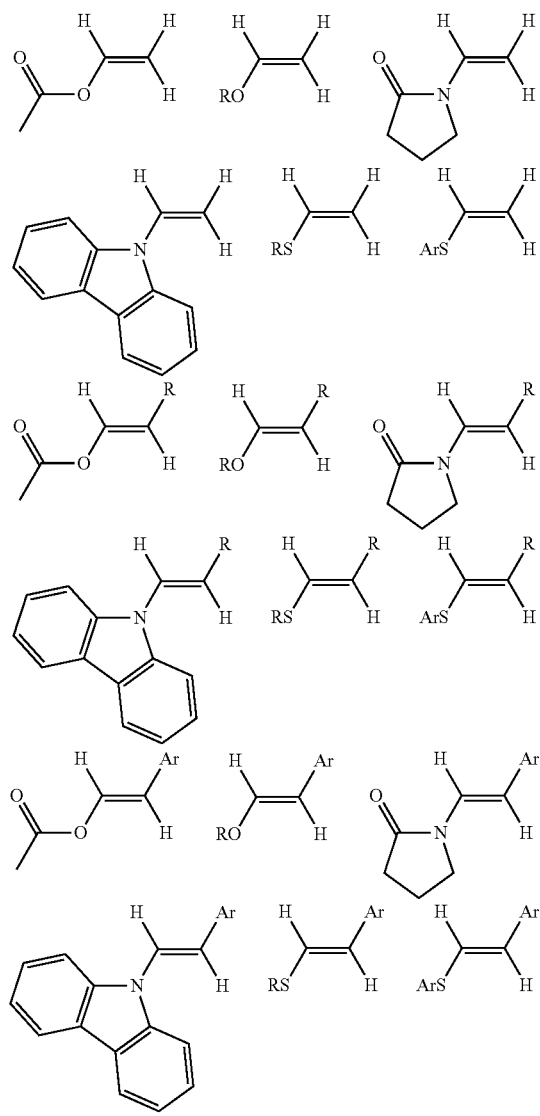

[Chem. 3]

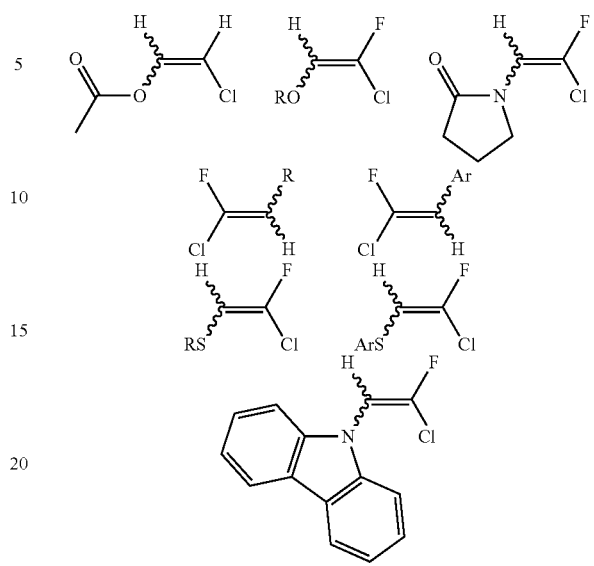

[9]
The production method according to any one of the above [1] to [8], wherein the olefin compound represented by the formula (31) is an olefin compound having a heteroatom existing adjacent to a carbon atom of the olefin.

[10]
The production method according to the above [9], wherein the heteroatom is an oxygen atom or a nitrogen atom.

[11]
The production method according to any one of the above [1] to [10], wherein at least one kind of an olefin compound selected from olefin compounds represented by the following formulae is produced as the compound represented by the formula (51) and the compound represented by the formula (52).

In the following formulae, R is an alkyl group having a carbon number of from 1 to 12 or an alkyl group having a carbon number of from 1 to 12 and having an etheric oxygen atom between a carbon atom and a carbon atom, and Ar is an aryl group having a carbon number of from 5 to 12.

[12]
The production method according to any one of the above [1] to [11], wherein a temperature at the time of performing the reaction of the olefin compound represented by the formula (21) with the olefin compound represented by the formula (31) is from 0 to 150° C.

[13]
The production method according to any one of the above [1] to [12], wherein no solvent is used.

Effect of the Invention

According to the production method for olefins containing chlorine and fluorine of the present invention, other olefins containing chlorine and fluorine can be simply and efficiently produced from industrially-easily-available olefins containing chlorine and fluorine such as R-1112, i.e., 1,2-dichloro-1,2-difluoroethylene, or R-1131a, i.e., 1-chloro-1-fluoroethylene, through olefin metathesis.

The present invention is described in detail hereinunder, but the present invention is not limited to the following embodiments. Within a range not overstepping the scope thereof, the present invention may be carried out in any modifications. In addition, the present invention relates to olefin metathesis with a metal catalyst, and description of general features common to those in conventional techniques may be omitted hereunder.

In this description, "a compound represented by a formula (X)" may be simply referred to as "a compound (X)".

Also in this description, the wording "1-chloro-1-fluoro-2-substituted olefins and the like" encompasses both 1-chloro-1-fluoro-2-substituted olefins and 1-chloro-1-fluoro-2,2-disubstituted olefins. The "1-chloro-1-fluoro-2-substituted olefin" means an olefin in which one chlorine atom and one fluorine atom bond to one carbon atom of the double bond and one hydrogen atom and one organic group bond to the other carbon atom. The "1-chloro-1-fluoro-2,2-di-substituted olefin" means an olefin in which one chlorine atom and one fluorine atom bond to one carbon atom of the double bond and the same two or different organic groups bond to the other carbon atoms.

The perhalogenated alkyl group means a group in which all hydrogen atoms of the alkyl group are substituted with halogen atoms. The perhalogenated alkoxy group means a group in which all hydrogen atoms of the alkoxy group are substituted with halogen atoms. The same shall apply to the perhalogenated alkoxy group and the perhalogenated aryl group.

The (per)halogenated alkyl group is used as a generic term including both a halogenated alkyl group and a perhalogenated alkyl group. That is, the group is an alkyl group having one or more halogen atoms. The same shall apply to the (per)halogenated alkoxy group, the (per)halogenated aryl group and the (per)halogenated aryloxy group.

The aryl group means a monovalent group corresponding to a residue derived by removing one hydrogen atom bonding to any one carbon atom in the carbon atoms forming an aromatic ring in an aromatic compound, and is used as a generic term including an aryl group derived from a carbocyclic compound and a heteroaryl group derived from a heterocyclic compound.

The carbon number of the hydrocarbon group means the total number of the carbon atoms contained in the whole of a hydrocarbon group, and in the case where the group does not have a substituent, the carbon number means the number of the carbon atoms forming the hydrocarbon group skeleton, while in the case where the group has a substituent, the carbon number means the sum of the number of the carbon atoms forming the hydrocarbon group skeleton and the number of the carbon atoms in the substituent.

<Reaction Mechanism>

The present invention relates to a production method for olefins containing chlorine and fluorine through olefin metathesis, and is, for example, characterized by including an intermediate (Metal-1) and an intermediate (Metal-2) as a part of the reaction mechanism thereof, as shown by the following scheme (a).

[Chem. 4]

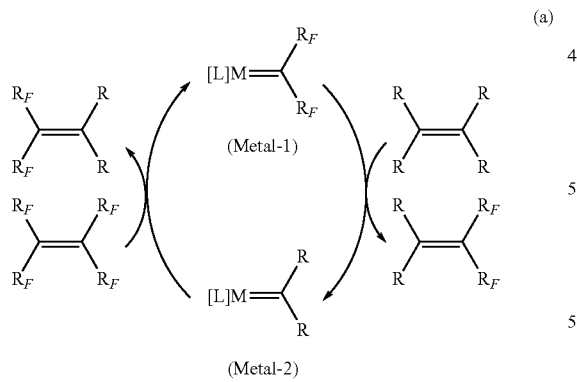

(a)

In the scheme (a), [L] is a ligand, M is ruthenium, molybdenum or tungsten, plural R's each are independently an organic group, and plural $R_F$'s each are independently a chlorine atom, fluorine atom or an organic group having at least one chlorine atom or fluorine atom therein.

Olefin metathesis reaction is reversible. That is, the scheme (a) includes a reversed reaction (reaction represented by an arrow in a reversed direction). However, detailed description of this point is omitted. Furthermore, the olefin to be produced may have geometric isomers. However, the detailed description of this point is omitted because it strongly depends on the individual reactions.

The present invention is, as shown by the following scheme (b), characterized in that, for example, a compound (21) is reacted with a compound (31) in the presence of a compound (11) to produce at least one selected from a compound (51) and a compound (52).

In the above-mentioned scheme, the compound (11) is described as a representative example of a ruthenium-carbene complex, molybdenum-carbene complex or a tungsten-carbene complex (hereinafter, these may be also referred to as "metal-carbene complex"). The metal-carbene complex may also be a compound (12), a compound (13), a compound (14), or a compound (15), and hereinafter the same shall apply to the metal-carbene complexes.

[Chem. 5]

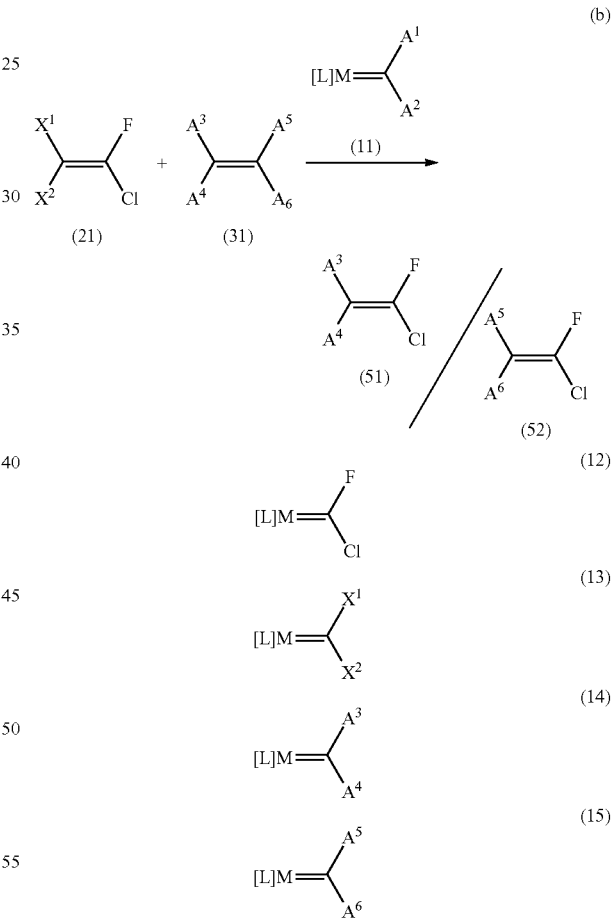

In this description, the symbols in formulae have the following meanings.

[L] is a ligand.

M is ruthenium, molybdenum or tungsten.

$A^1$ to $A^6$ are each independently a functional group selected from the group consisting of the following functional group (i), functional group (ii), functional group (iii), and functional group (iv). $A^1$ and $A^2$ may bond to each other to form a ring. $A^3$ and $A^4$ may bond to each other to form a ring. $A^5$ and $A^6$ may bond to each other to form a ring. In the case where one of $A^1$ or $A^2$ is a halogen atom, the other is a functional group selected from the group consisting of the functional group (i), the functional group (iii), and the functional group (iv). In the case where one of $A^3$ or $A^4$ is a halogen atom, the other is a functional group selected from the group consisting of the functional group (i), the functional group (iii), and the functional group (iv). In the case where one of $A^5$ or $A^6$ is a halogen atom, the other is a functional group selected from the group consisting of the functional group (i), the functional group (iii), and the functional group (iv).

$X^1$ and $X^2$ are each independently a functional group selected from the group consisting of the following functional group (i), functional group (ii), functional group (v), and functional group (vi), and may bond to each other to form a ring.

Functional groups (i) to (vi) respectively have the following meanings.

Functional group (i): a hydrogen atom.

Functional group (ii): a halogen atom.

Functional group (iii): a monovalent hydrocarbon group having a carbon number of from 1 to 20.

Functional group (iv): a monovalent hydrocarbon group having a carbon number of from 1 to 20 and containing one or more atoms selected from the group consisting of a halogen atom, an oxygen atom, a nitrogen atom, a sulfur atom, a phosphorus atom, and a silicon atom.

Functional group (v): a functional group selected from the group consisting of an alkyl group having a carbon number of from 1 to 12, an alkoxy group having a carbon number of from 1 to 12, an aryl group having a carbon number of from 5 to 20, an aryloxy group having a carbon number of from 5 to 20, a (per)halogenated alkyl group having a carbon number of from 1 to 12, a (per)halogenated alkoxy group having a carbon number of from 1 to 12, a (per)halogenated aryl group having a carbon number of from 5 to 20, and a (per)halogenated aryloxy group having a carbon number of from 5 to 20.

Functional group (vi): the functional group (v) containing one or more atoms selected from the group consisting of an oxygen atom, a nitrogen atom, a sulfur atom, a phosphorus atom, and a silicon atom.

The olefin metathesis in the present invention can be expressed as a series of cycle reactions. The cycle reactions can be represented, for example, by the following scheme (I). In the following scheme (I), R represents an organic group and examples thereof include alkyl groups such as butyl group. The following scheme (I) includes upper and lower two cycles. Of the two cycles, one cycle alone may occur or both the two cycles may competitively occur, depending on the combination of the olefin compounds to be supplied in the system.

[Chem. 6]

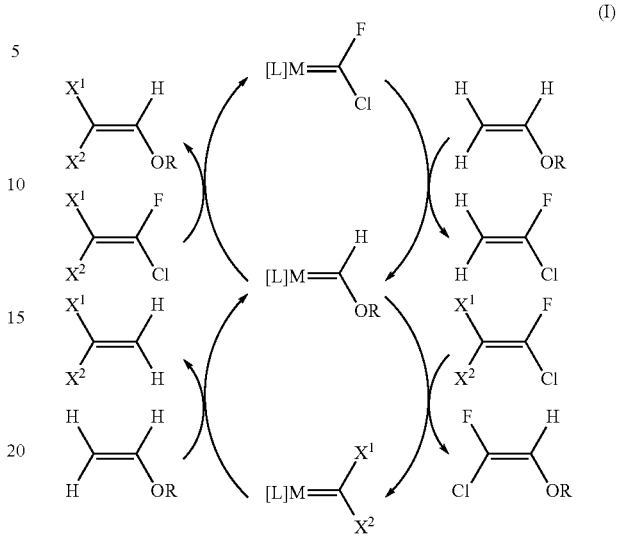

In the present invention, the reaction is performed in the presence of at least one kind of compound selected from the group consisting of a compound (11), a compound (12), a compound (13), a compound (14), and a compound (15) (hereinafter, these may also referred to as "metal catalyst").

As the metal catalyst, the compound (11) is preferable at the start of the reaction from the viewpoint of availability and reaction efficiency.

<Compound (11)>

The metal catalyst such as a compound (11), serves as a catalyst in the production method according to the present invention and means both one charged as a reagent and one formed during the reaction (catalytically active species). Here, as the compound (11), known are both one that comes to exhibit catalytic activity through dissociation of some ligands under the reaction condition, and one that exhibits catalytic activity with no dissociation of ligands, and any of these is employable in the present invention with no limitation. In general, olefin metathesis proceeds with repeating olefin coordination and dissociation with and from catalyst, and therefore during reaction, it is not always definite how many ligands except olefin could coordinate on the catalyst. Consequently, in this description, [L] does not specifically define the number and the type of ligand.

$A^1$ and $A^2$ in the compound (11) are each independently a hydrogen atom, a halogen atom, a monovalent hydrocarbon group having a carbon number of from 1 to 20, or a monovalent hydrocarbon group having a carbon number of from 1 to 20 and containing one or more atoms selected from the group consisting of a halogen atom, an oxygen atom, a nitrogen atom, a sulfur atom, a phosphorus atom, and a silicon atom, and may bond to each other to form a ring. The case where both $A^1$ and $A^2$ are halogen atoms is excluded from the compound (11).

Examples of the halogen atoms include a fluorine atom, a chlorine atom, a bromine atom, and an iodine atom and the fluorine atom and the chlorine atom are preferred from the viewpoint of availability.

The monovalent hydrocarbon group having a carbon number of from 1 to 20 is preferably an alkyl group having a carbon number of from 1 to 20 or an aryl group having a carbon number of from 5 to 20, and may be linear, branched, or cyclic.

Preferred examples of the monovalent hydrocarbon group having a carbon number of from 1 to 20 and containing one or more atoms selected from the group consisting of a halogen atom, an oxygen atom, a nitrogen atom, a sulfur atom, a phosphorus atom, and a silicon atom include alkyl groups having a carbon number of from 1 to 20 and containing the atoms, alkoxy groups having a carbon number of from 1 to 20, aryl groups having a carbon number of from 5 to 20 and containing the atoms, and aryloxy groups having a carbon number of from 5 to 20. This monovalent hydrocarbon group may be linear, branched, or cyclic. In these preferred groups, a halogen atom may bond to at least a part of the carbon atoms. Namely, the group may be, for example, a (per)fluoroalkyl group or a (per)fluoroalkoxy group. These preferred groups each may have an etheric oxygen atom between a carbon atom and a carbon atom. Furthermore, these preferred groups each may have a substituent containing one or more atoms selected from the group consisting of a halogen atom, an oxygen atom, a nitrogen atom, a sulfur atom, a phosphorus atom, and a silicon atom. Examples of the substituent include a hydroxyl group, an amino group, an imino group, a nitrile group, an amido group (a carbonylamino group), a carbamate group (an oxycarbonylamino group), a nitro group, a carboxyl group, an ester group (an acyloxy group or alkoxycarbonyl group), a thioether group, and a silyl group, and the like. These groups may be further substituted with an alkyl group or an aryl group. For example, the amino group (—NH$_2$) may be a monoalkylamino group (—NHR), a monoarylamino group (—NHAr), a dialkylamino group (—NR$_2$), or a diarylamino group (—NAr$_2$). R is an alkyl group having a carbon number of from 1 to 12 or an alkyl group having a carbon number of from 1 to 12 and having an etheric oxygen atom between a carbon atom and a carbon atom, and Ar is an aryl group having a carbon number of from 5 to 12.

Preferred examples of the compound (11) having a combination of these $A_1$ and $A_2$ include one represented by the following formula, from the viewpoint of the availability thereof. In the following formulae, Cy represents a cyclohexyl group.

[Chem. 7]

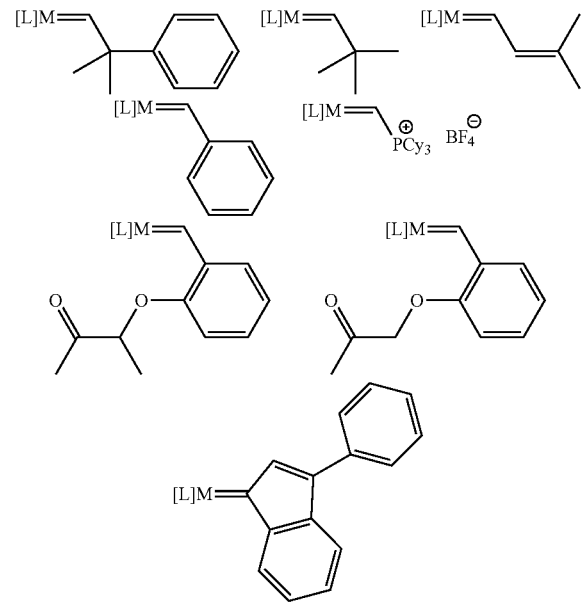

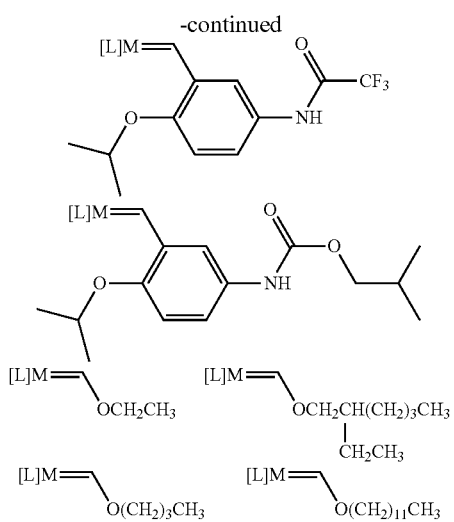

It is preferable in the present invention that the metal of the metal catalyst should be ruthenium.

Specifically, in the case where M in the compound (11) is ruthenium, the compound can be represented by the following formula (11-A). The ligand [L] in the formula (11) is represented by $L^1$, $L^2$, $L^3$, $Z^1$, and $Z^2$ in the formula (11-A). The positions of $L^1$, $L^2$, $L^3$, $Z^1$, and $Z^2$ are not limited, and may be alternated to each other in the formula (11-A). That is, $Z^1$ and $Z^2$, for example, may be at the trans-position or at the cis-position.

[Chem. 8]

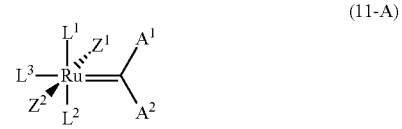

(11-A)

In the formula (11-A), $L^1$, $L^2$, and $L^3$ are each independently a ligand that has a neutral charge when dissociated from the central metal (a neutral electron-donating ligand). Concretely, there are mentioned a carbonyl group, amines, imines, pyridines, ethers, nitriles, esters, phosphines, thioethers, sulfoxides, sulfones, aromatic compounds, olefins, isocyanides, thiocyanates, heteroatom-containing carbene compounds, and the like. Of those, preferred are phosphines, pyridines and heteroatom-containing carbene compounds, and more preferred are trialkyl phosphines and N-heterocyclic carbene compounds.

However, depending on the combination of the abovementioned ligands, all ligands could not coordinate with the metal center owing to steric factors and/or electronic factors, and as a result, some coordination positions may be vacant sites. For example, $L^1$, $L^2$, and $L^3$ include the following combinations. $L^1$: a heteroatom-containing carbene compound, $L^2$: a phosphine, and $L^3$: vacant (vacant coordination cite). $L^1$: a heteroatom-containing carbene compound, $L^2$: a pyridine, and $L^3$: a pyridine.

In formula (11-A), $Z^1$ and $Z^2$ are each independently a ligand that has a negative charge when dissociated from the central metal (anionic ligand). Concretely, there are mentioned a halogen atom, a hydrogen atom, a substituted diketonate group, a substituted cyclopentadienyl group, an alkyl group having a carbon number of from 1 to 20, an aryl group having a carbon number of from 5 to 20, a substituted alkoxy group having a carbon number of from 1 to 20, a substituted aryloxy group having a carbon number of from 5 to 20, a substituted carboxylate group having a carbon number of from 1 to 20, a substituted arylcarboxylate group having a carbon number of from 6 to 20, a substituted alkylthiolate group having a carbon number of from 1 to 20, a substituted arylthiolate group having a carbon number of from 6 to 20, a nitrate group, and the like. Above all, preferred is a halogen atom, and more preferred is a chlorine atom.

In the formula (11-A), $A^1$ and $A^2$ are respectively the same as the $A^1$ and $A^2$ in the formula (11).

From 2 to 6 of $L^1$, $L^2$, $L^3$, $Z^1$, $Z^2$, $A^1$, and $A^2$ may bond to each other to form a polydentate ligand.

The above-mentioned catalyst is generally referred to as "ruthenium-carbene complex", and, for example, ruthenium-carbene complexes described in Vougioukalakis, G. C. et al., *Chem. Rev.*, 2010, 110, 1746-1787 can be used. Also for example, ruthenium-carbene complexes commercially available from Aldrich or Umicore are also usable.

Specific examples of the ruthenium-carbene complex include bis(triphenylphosphine)benzylidene ruthenium dichloride, bis(tricyclohexylphosphine)benzylidene ruthenium dichloride, bis(tricyclohexylphosphine)-3-methyl-2-butenylidene ruthenium dichloride, (1,3-diisopropylimidazol-2-ylidene)(tricyclohexylphosphine)benzylidene ruthenium dichloride, (1,3-dicyclohexylimidazol-2-yldene)(tricyclohexylphosphine)benzylidene ruthenium dichloride, (1,3-dimesitylimidazol-2-ylidene)(tricyclohexylphosphine)benzylidene ruthenium dichloride, (1,3-dimesityl-4,5-dihydroimidazol-2-ylidene)(tricyclohexylphosphine)benzylidene ruthenium dichloride, [1,3-bis(2,6-diisopropylphenyl)-4,5-dihydroimidazol-2-ylidene](tricyclohexylphosphine)benzylidene ruthenium dichloride, [1,3-bis(2-methylphenyl)-4,5-dihydroimidazol-2-ylidene](tricyclohexylphosphine)benzylidene ruthenium dichloride, [1,3-dicyclohexyl-4,5-dihydroimidazol-2-ylidene](tricyclohexylphosphine)benzylidene ruthenium dichloride, bis(tricyclohexylphosphine)ethoxymethylidene ruthenium dichloride, (1,3-dimesityl-4,5-dihydroimidazol-2-ylidene)(tricyclohexylphosphine)ethoxymethylidene ruthenium dichloride, (1,3-dimesityl-4,5-dihydroimidazol-2-ylidene)[bis(3-bromopyridine)]benzylidene ruthenium dichloride, (1,3-dimesityl-4,5-dihydroimidazol-2-ylidene)(2-isopropoxyphenylmethylidene) ruthenium dichloride, (1,3-dimesityl-4,5-dihydroimidazol-2-ylidene)[(tricyclohexylphosphoranyl)methylidene]dichlororuthenium tetrafluoroborate, UmicoreM2, UmicoreM51, UmicoreM52, UmicoreM71 SIMes, UmicoreM71 SIPr, UmicoreM73 SIMes, UmicoreM73 SIPr, and the like. Especially preferred are (1,3-dimesityl-4,5-dihydroimidazol-2-ylidene)(tricyclohexylphosphine)benzylidene ruthenium dichloride, (1,3-dimesityl-4,5-dihydroimidazol-2-ylidene)(2-isopropoxyphenylmethylidene) ruthenium dichloride, (1,3-dimesityl-4,5-dihydroimidazol-2-ylidene)[(tricyclohexylphosphoranyl)methylidene] dichlororuthenium tetrafluoroborate, UmicoreM51, UmicoreM52, UmicoreM71SIMes, UmicoreM71 SIPr, UmicoreM73 SIMes, and UmicoreM73SIPr. Of the above-mentioned complexes, the names starting from "Umicore" are trade names of the products by Umicore.

The above-mentioned ruthenium-carbene complexes may be used either singly or used in combination of two or more kinds thereof. Further if desired, these may be used as immobilized by a carrier such as silica gel, alumina, polymer or the like.

In the case where M in the compound (11) is molybdenum or tungsten, the compound (11) can be represented by the following formula (11-B) or formula (11-C). The compound (11) may be ones to which a coordination solvent (e.g., tetrahydrofuran, ethylene glycol dimethyl ether and the like) further coordinates.

In the case where the metal of the metal catalyst is molybdenum or tungsten, it is preferable that the ligand [L] of the metal catalyst should include an imide ligand ($R^1$—N=M). Examples of $R^1$ include an alkyl group and an aryl group. Also as the ligand [L] of the metal catalyst, a ligand including two coordinating oxygen atoms is preferable. The term "a ligand including two coordinating oxygen atoms" means both cases, that is, the case where a ligand having two or more oxygen atoms coordinates by two of the oxygen atoms thereof and the case where two monodentate ligands each having an oxygen atom coordinate (these monodentate ligands may be the same or different).

[Chem. 9]

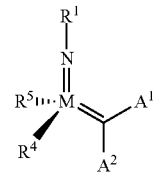

(11-B)

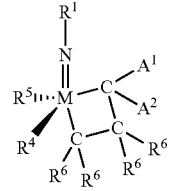

(11-C)

The ligand [L] in the formula (11) is represented by =$NR^1$, —$R^4$, and —$R^5$ in formula (11-B). The position of the =$NR^1$, —$R^4$, and —$R^5$ is not limited, and may be replaced with each other in the formula (11-B). M is molybdenum or tungsten, and examples of $R^1$ include an alkyl group and an aryl group. Examples of $R^4$ and $R^5$ include a halogen atom, an alkyl group, an aryl group, an alkoxy group, an aryloxy group, a sulfonate group, an amino group (such as alkylamino groups, $\eta^1$-pyrrolido, and $\eta^5$-pyrrolido), and the like. $R^4$ and $R^5$ may be linked to each other to be a bidentate ligand.

The formula (11-C) is a compound in which an olefin ($C_2(R^6)_4$) has added through cycloaddition ([2+2] cycloaddition) to the metal-carbon double bond moiety of a compound represented by the formula (11-B) to form a metal-lacyclobutane ring. The four $R^6$'s respectively are monovalent functional groups which may be the same or different, and examples thereof include a hydrogen atom, a halogen atom, an aryl group, an alkoxy group, an aryloxy group, and an amino group. A compound represented by the formula (11-C) is considered to be equivalent to a compound represented by the formula (11-B).

In the formula (11-B) and formula (11-C), $A^1$ and $A^2$ are respectively the same as the $A^1$ and $A^2$ in the formula (11).

The above-mentioned catalyst is generally referred to as a "molybdenum-carbene complex" or "tungsten-carbene complex", and for example, the molybdenum-carbene complexes or tungsten-carbene complexes described in Grela, K.

(Ed), *Olefin Metathesis: Theory and Practice*, Wiley, 2014 can be used. Also for example, molybdenum-carbene complexes or tungsten-carbene complexes commercially available from Aldrich Co., Strem Inc., or XiMo AG.

The above-mentioned molybdenum-carbene complexes or tungsten-carbene complexes may be used either singly or in combination of two or more kinds thereof. Further if desired, these may be used as immobilized by a carrier such as silica gel, alumina, polymer or the like.

Specific examples of the compound (11-B) is shown below. Me means a methyl group, i-Pr means an isopropyl group, t-Bu means a tertiary butyl group, and Ph means a phenyl group, respectively.

[Chem. 10]

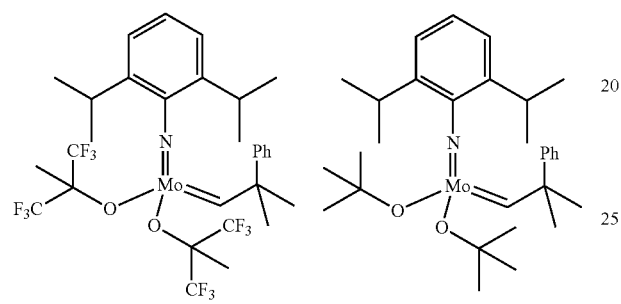

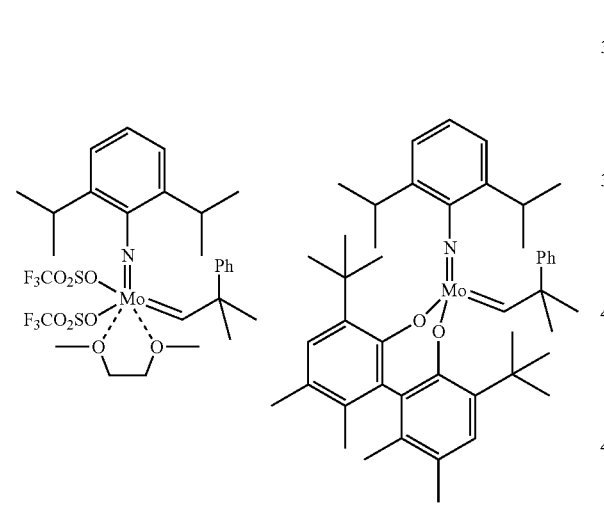

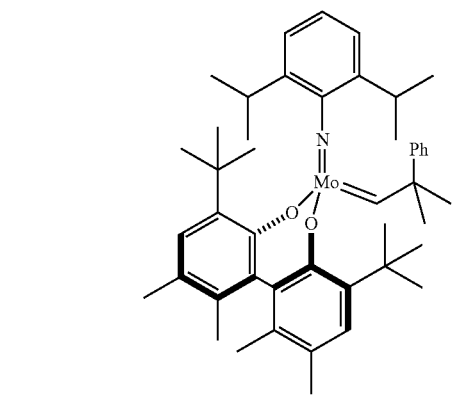

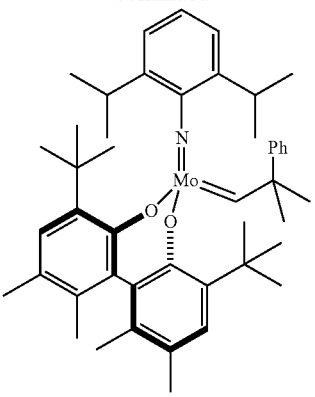

[Chem. 11]

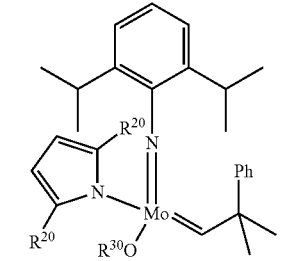

$R^{20}$ = H, $R^{30}$ = t-Bu, i-Pr, 2,6-i-PrC$_6$H$_3$, CH(CF$_3$)$_2$, C(Me)(CF$_3$)$_2$; $R^{20}$ = Me, $R^{30}$ = C(Me)(CF$_3$)$_2$

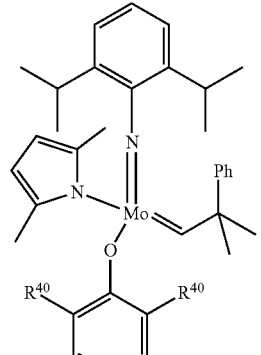

$R^{40}$ = 2,4,6-Me$_3$C$_8$H$_2$, 2,4,6-i-Pr$_3$C$_8$H$_2$

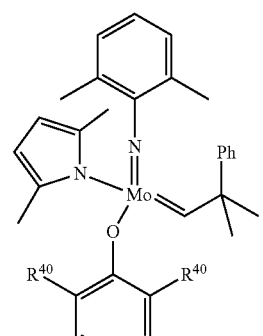

$R^{40}$ = 2,4,6-Me$_3$C$_8$H$_2$, 2,4,6-i-Pr$_3$C$_8$H$_2$

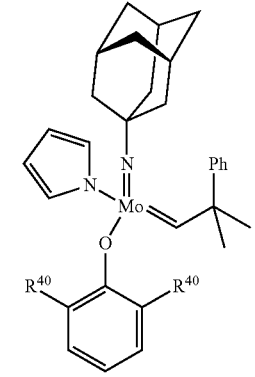

$R^{40}$ = 2,4,6-Me$_3$C$_8$H$_2$, 2,4,6-i-Pr$_3$C$_8$H$_2$

-continued
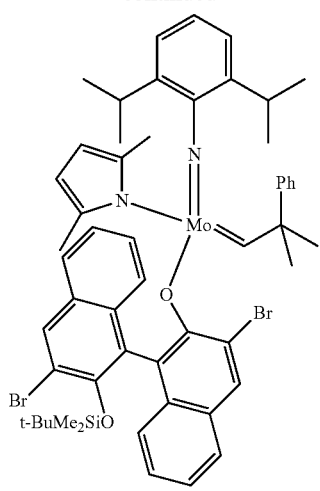
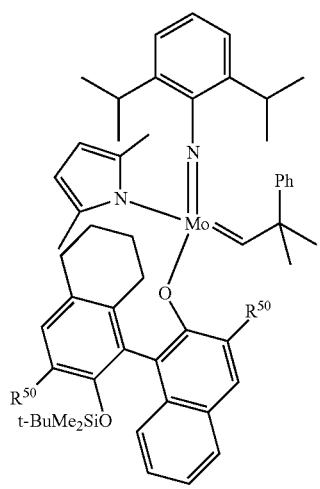
R⁵⁰ = Br, Cl
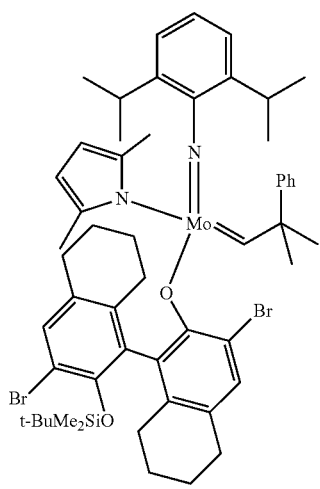
-continued
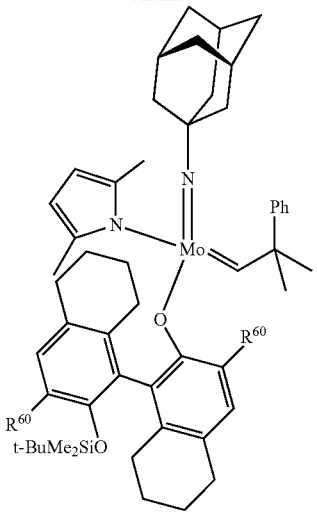
R⁶⁰ = Br, Cl, I, F
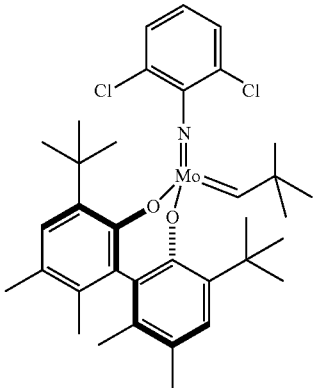
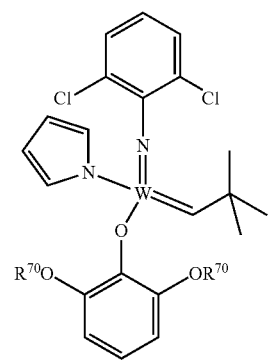
R⁷⁰ = 2,4,6-i-Pr₃C₆H₂
Specific examples of the compound (11-C) include the following compound.

[Chem. 12]

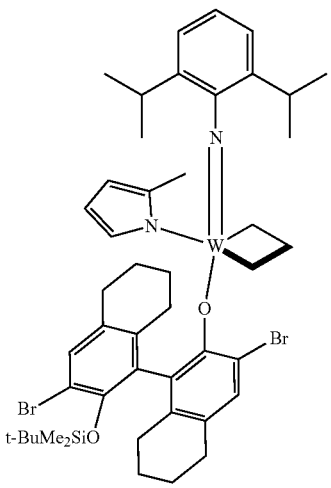

<Compounds (12) to (15)>

The compounds (12) to (15), like the compound (11), serves as a catalyst in the production method according to the present invention and means both one charged as a reagent and one formed during the reaction (catalytically active species).

[Chem. 13]

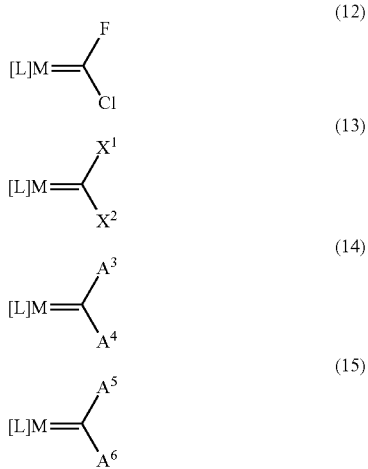

In the formulae (12) to the formula (15), [L], M, $X^1$, $X^2$, and $A^3$ to $A^6$ have the same meanings as defined above.

<Compound (21)>

$X^1$ and $X^2$ in the compound (21) have the same meanings as defined above.

That is, the compound (21) is an olefin compound in which one chlorine atom and one fluorine atom are bonding to one of the carbon atoms constituting the double bond and which has the partial structure [C(Cl)F=C].

Examples of the halogen atom include a fluorine atom, a chlorine atom, a bromine atom, or an iodine atom and a fluorine atom or a chlorine atom is preferred from the viewpoint of availability.

The alkyl group having a carbon number of from 1 to 12 is preferably the group having a carbon number of from 1 to 8, and specifically, a methyl group, an ethyl group, or a propyl group is preferred from the viewpoint of availability. The alkyl group chain may be linear, branched, or cyclic.

The alkoxy group having a carbon number of from 1 to 12 is preferably an alkoxy group having a carbon number of from 1 to 8. Specifically, a methoxy group, an ethoxy group, or a propoxy group is preferred from the viewpoint of availability. The alkoxy group chain may be linear, branched, or cyclic.

The aryl group having a carbon number of from 5 to 20 is preferably the group having a carbon number of from 5 to 12. Specifically, a phenyl group is preferred from the viewpoint of availability.

The aryloxy group having a carbon number of from 5 to 20 is preferably an aryloxy group a carbon number of from 5 to 12. Specifically, a phenyloxy group is preferred from the viewpoint of availability.

The (per)halogenated alkyl group having a carbon number of from 1 to 12 is preferably the group having a carbon number of from 1 to 8. In particular, a (per)fluoroalkyl group having a carbon number of from 1 to 8 is preferred. Specifically, a trifluoromethyl group, a pentafluoroethyl group, or a heptafluoropropyl group is preferred from the viewpoint of availability. The alkyl group chain may be linear, branched, or cyclic.

The (per)halogenated alkoxy group having a carbon number of from 1 to 12 is preferably the group having a carbon number of from 1 to 8. In particular, a (per)fluoroalkoxy group having a carbon number of from 1 to 8 is preferred. Specifically, a trifluoromethoxy group, a pentafluoroethoxy group, a heptafluoropropoxy group, a perfluoro(methoxymethoxy) group, or a perfluoro(propoxypropoxy) group is preferred. In particular, a trifluoromethoxy group or a perfluoro(propoxypropoxy) group is preferred from the viewpoint of availability. The alkoxy group chain may be linear, branched, or cyclic.

The (per)halogenated aryl group having a carbon number of from 5 to 20 is preferably the group having a carbon number of from 5 to 12, and is especially preferably a (per)fluoroaryl group having a carbon number of from 5 to 12. Specifically, a monofluorophenyl group or a pentafluorophenyl group is preferred. In particular, a pentafluorophenyl group is preferred from the viewpoint of availability.

The (per)halogenated aryloxy group having a carbon number of from 5 to 20 is preferably the group having a carbon number of from 5 to 12, and is especially preferably a (per)fluoroaryloxy group having a carbon number of from 5 to 12. Specifically, a monofluorophenyloxy group or a pentafluorophenyloxy group is preferred. In particular, a pentafluorophenyloxy group is preferred from the viewpoint of availability.

The alkyl group, alkoxy group, aryl group, aryloxy group, (per)halogenated alkyl group, (per)halogenated alkoxy group, (per)halogenated aryl group, or (per)halogenated aryloxy group may have a substituent containing one or more atoms selected from the group consisting of an oxygen atom, a nitrogen atom, a sulfur atom, a phosphorus atom, and a silicon atom. Examples of the substituent include a nitrile group, a carboxyl group, and an ester group (an acyloxy group or an alkoxycarbonyl group). Even in the case where these groups have the substituent, the total number of carbon atoms in each of the alkyl group, alkoxy group, (per)halogenated alkyl group, and (per)halogenated alkoxy group is from 1 to 12, and the total number of carbon atoms of each of the aryl group, aryloxy group, (per)halogenated aryl group, and (per)halogenated aryloxy group is from 5 to 20.

The alkyl group, alkoxy group, aryl group, aryloxy group, (per)halogenated alkyl group, (per)halogenated alkoxy group, (per)halogenated aryl group, or (per)halogenated aryloxy group may have an etheric oxygen atom between a carbon atom and a carbon atom. That is, it is preferable that the functional group (vi) should be the functional group (v) having one or more oxygen atoms, and it is more preferable that the oxygen atom should be an etheric oxygen atom. Namely, it is preferable that the functional group (vi) should be the following functional group (vii). Functional group (vii): the functional group (v) having an etheric oxygen atom between a carbon atom and a carbon atom.

A preferred combination of $X^1$ and $X^2$ is one where $X^1$ is the functional group (i), functional group (ii), functional group (v), or functional group (vii) and $X^2$ is the functional group (ii), functional group (v), or functional group (vii).

A more preferred combination is one where $X^1$ is a hydrogen atom, a halogen atom, a (per)halogenated alkyl group having a carbon number of from 1 to 12, a (per)halogenated alkyl group having a carbon number of from 1 to 12 and having an etheric oxygen atom between a carbon atom and a carbon atom, a (per)halogenated alkoxy group having a carbon number of from 1 to 12, a (per)halogenated alkoxy group having a carbon number of from 1 to 12 and having an etheric oxygen atom between a carbon atom and a carbon atom, a (per)halogenated aryl group having a carbon number of from 5 to 20, a (per)halogenated aryl group having a carbon number of from 5 to 20 and having an etheric oxygen atom between a carbon atom and a carbon atom, a (per)halogenated aryloxy group having a carbon number of from 5 to 20, or a (per)halogenated aryloxy group having a carbon number of from 5 to 20 and having an etheric oxygen atom between a carbon atom and a carbon atom; and $X^2$ is a halogen atom, an alkyl group having a carbon number of from 1 to 12, an alkyl group having a carbon number of from 1 to 12 and having an etheric oxygen atom between a carbon atom and a carbon atom, an alkoxy group having a carbon number of from 1 to 12, an alkoxy group having a carbon number of from 1 to 12 and having an etheric oxygen atom between a carbon atom and a carbon atom, an aryl group having a carbon number of from 5 to 20, an aryl group having a carbon number of from 5 to 20 and having an etheric oxygen atom between a carbon atom and a carbon atom, a (per)halogenated alkyl group having a carbon number of from 1 to 12, a (per)halogenated alkyl group having a carbon number of from 1 to 12 and having an etheric oxygen atom between a carbon atom and a carbon atom, a (per)halogenated alkoxy group having a carbon number of from 1 to 12, a (per)halogenated alkoxy group having a carbon number of from 1 to 12 and having an etheric oxygen atom between a carbon atom and a carbon atom, a (per)halogenated aryl group having a carbon number of from 5 to 20, a (per)halogenated aryl group having a carbon number of from 5 to 20 and having an etheric oxygen atom between a carbon atom and a carbon atom, a (per)halogenated aryloxy group having a carbon number of from 5 to 20, or a (per)halogenated aryloxy group having a carbon number of from 5 to 20 and having an etheric oxygen atom between a carbon atom and a carbon atom.

Preferred examples of the compound (21) include 1-chloro-1-fluoroethylene, 1,2-dichloro-1,2-difluoroethylene, or 1,3,3-trichloro-1,2,3-trifluoropropene. However, in the case where there are E/Z isomers, the compound (21) may be either of the isomers. As the compound (11), only one kind thereof may be used, or two or more kinds thereof may be used in combination. However, since by-products are prone to be produced in a large amount, it is preferred to use only one kind More preferably, the compound (21) is 1-chloro-1-fluoroethylene or 1,2-dichloro-1,2-difluoroethylene.

$A^3$ to $A^6$ in the compound (31) have the same meanings as defined above. That is, $A^3$ to $A^6$ are each independently a hydrogen atom, a halogen atom, a monovalent hydrocarbon group having a carbon number of from 1 to 20, or a monovalent hydrocarbon group having a carbon number of from 1 to 20 and containing one or more atoms selected from the group consisting of a halogen atom, an oxygen atom, a nitrogen atom, a sulfur atom, a phosphorus atom, and a silicon atom.

$A^3$ and $A^4$ may bond to each other to form a ring. $A^5$ and $A^6$ may bond to each other to form a ring. The ring preferably is a ring containing carbon atoms only or containing a carbon atom and a heteroatom. Examples of the size of the ring include a 3-membered ring to a 10-membered ring. Examples of the partial structure of the ring include the structure of the following formula.

[Chem. 14]

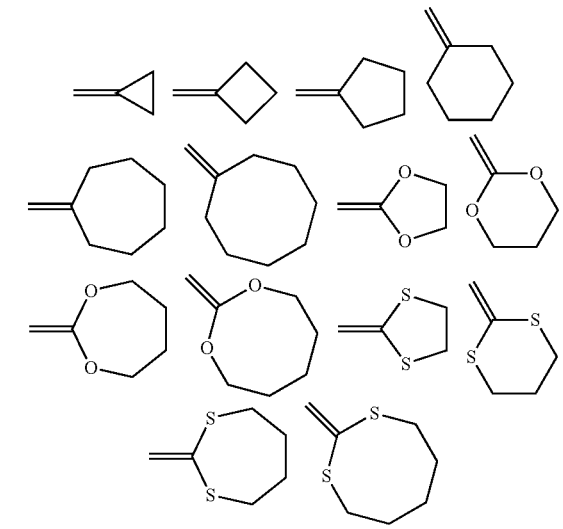

In the case where $A^3$ and $A^4$ are both halogen atoms and/or $A^5$ and $A^6$ are both halogen atoms is excluded from the compound (31). That is, although the compound (31) is an olefin compound, the compound does not include a 1,1-dihalogenoolefin.

Examples of the halogen atom include a fluorine atom, a chlorine atom, a bromine atom, and an iodine atom and from the viewpoint of availability, a fluorine atom and a chlorine atom are preferred.

The monovalent hydrocarbon group having a carbon number of from 1 to 20 is preferably an alkyl group having a carbon number of from 1 to 20, an alkoxy group having a carbon number of from 1 to 20, an aryl group having a carbon number of from 5 to 20, or an aryloxy group having a carbon number of from 5 to 20. Especially preferred from the viewpoint of availability is a methyl group, an ethyl group, a propyl group, a phenyl group, a methoxy group, an ethoxy group, a propoxy group, an isopropoxy group, a butoxy group, a tert-butoxy group, a (2-ethyl)hexyloxy group, or a dodecyloxy group. The hydrocarbon group skeleton may be linear, branched, or cyclic.

Preferred examples of the monovalent hydrocarbon group having a carbon number of from 1 to 20 and containing one or more atoms selected from the group consisting of a halogen atom, an oxygen atom, a nitrogen atom, a sulfur atom, a phosphorus atom, and a silicon atom include an alkyl group having a carbon number of from 1 to 20 and containing the atom, an alkoxy group having a carbon number of from 1 to 20 and containing the atom, an aryl group having a carbon number of from 5 to 20 and containing the atom, and an aryloxy group having a carbon number of from 5 to 20 and containing the atom. In these preferred groups, a halogen atom may bond to at least a part of the carbon atoms. That is, the group may be, for example, a (per) fluoroalkyl group or a (per)fluoroalkoxy group. These preferred groups each may have an etheric oxygen atom between a carbon atom and a carbon atom. Furthermore, these preferred groups may have a substituent having an oxygen atom, a nitrogen atom, a sulfur atom, a phosphorus atom, or a silicon atom. Examples of the substituent include an amino group, a nitrile group, a carboxyl group, an ester group (an acyloxy group or an alkoxycarbonyl group), a thioalkyl group, and a silyl group.

From the viewpoint of availability, it is especially preferable that $A^3$ to $A^6$ should be each independently a hydrogen atom, a phenyl group, a methoxy group, an ethoxy group, a propoxy group, an isopropoxy group, a butoxy group, a tert-butoxy group, a (2-ethyl)hexyloxy group, a dodecyloxy group, an acetyl group, a trifluoromethyl group, a pentafluoroethyl group, a heptafluoropropyl group, a perfluorobutyl group, a perfluorohexyl group, or a perfluorooctyl group. Of the compound (31), a compound having a heteroatom in the vinyl position (a compound where an atom except for a carbon atom or a hydrogen atom is existing adjacent to a carbon atom of the olefin) is thought to have the effect of stabilizing an intermediate generated during the reaction and to thereby render the olefin metathesis apt to proceed. Consequently, the compound (31) having a heteroatom in the vinyl position is preferred. The heteroatom preferably existing adjacent to a carbon atom of the olefin is preferably an oxygen atom, a nitrogen atom, a sulfur atom, a halogen atom, a phosphorus atom, or a silicon atom, more preferably is an oxygen atom, a nitrogen atom, or a halogen atom, and especially preferably is an oxygen atom or a nitrogen atom.

As the compound (31), both a terminal olefin and an internal olefin can be utilized. There is no particular limitation on the number of the substituent on the double bond, however, ethylene, a mono-substituted olefin, and a 1,2-disubstituted olefin are preferred since these compounds have high reactivity. There also are no particular limitations on the geometrical isomerism on the double bond.

A preferred combination of $A^3$ and $A^4$ includes one where $A^3$ is a hydrogen atom; and $A^4$ is a hydrogen atom, a monovalent hydrocarbon group having a carbon number of from 1 to 20, or a monovalent hydrocarbon group having a carbon number of from 1 to 20 and containing one or more atoms selected from the group consisting of a halogen atom, an oxygen atom, a nitrogen atom, a sulfur atom, a phosphorus atom, and a silicon atom.

A preferred combination of $A^5$ and $A^6$ includes one where $A^5$ is a hydrogen atom; and $A^6$ is a hydrogen atom, a monovalent hydrocarbon group having a carbon number of from 1 to 20, or a monovalent hydrocarbon group having a carbon number of from 1 to 20 and containing one or more atoms selected from the group consisting of a halogen atom, an oxygen atom, a nitrogen atom, a sulfur atom, a phosphorus atom, and a silicon atom.

More preferred examples of the compound (31) include the olefin compounds shown below.

[Chem. 15]

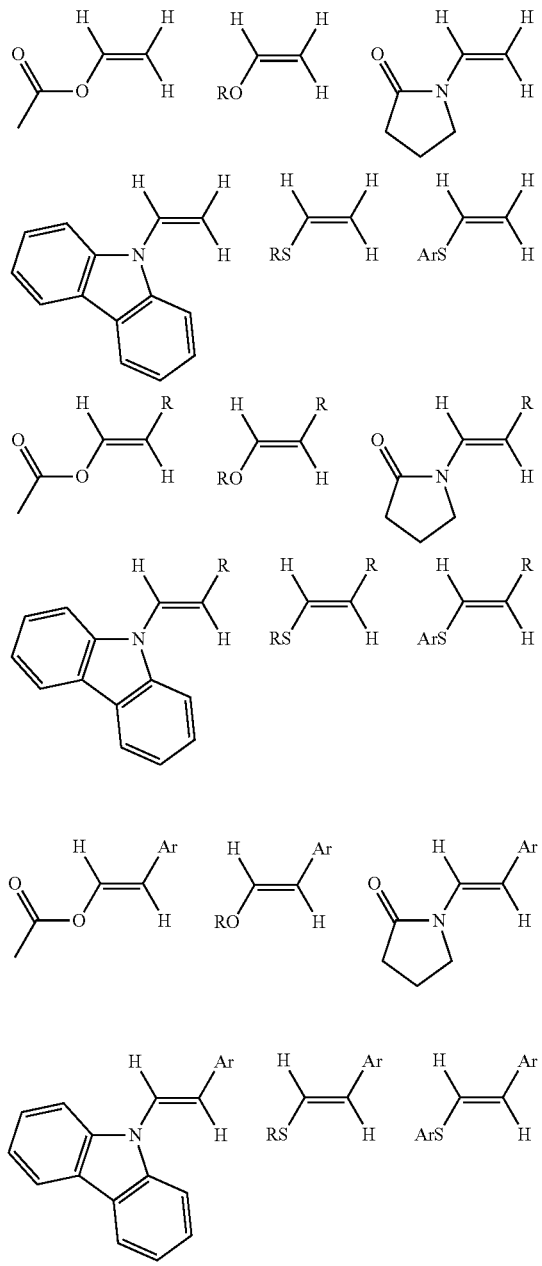

R in the above formulae is an alkyl group having a carbon number of from 1 to 12 or an alkyl group having a carbon number of from 1 to 12 and having an etheric oxygen atom between a carbon atom and a carbon atom. In the case where there are plural R's in the same molecule, the R's may be the same or different. Ar is an aryl group having a carbon number of from 5 to 12. In the case where there are plural Ar's in the same molecule, the Ar's may be the same or different.

Especially preferred of these examples of the compound (31) include the compounds shown below.

[Chem. 16]

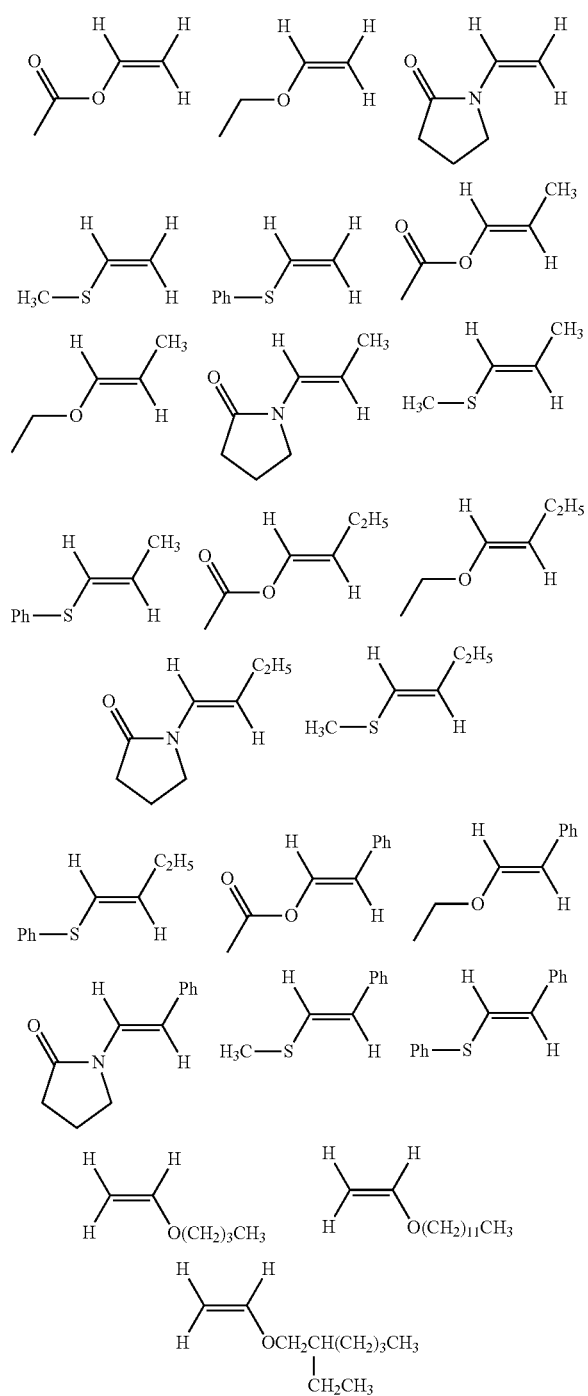

<Compounds (51) and (52)>

Examples of the chlorine-containing fluorine-containing compound (51) and compound (52) obtained by the olefin metathesis according to the present invention include the following compound. A wavy line indicates that the compound is either of E/Z isomers or is a mixture of both.

[Chem. 17]

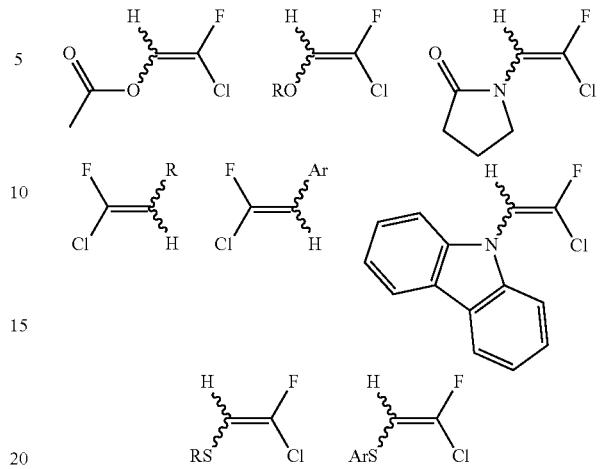

R in the above formula is an alkyl group having a carbon number of from 1 to 12 or an alkyl group having a carbon number of from 1 to 12 and having an etheric oxygen atom between a carbon atom and a carbon atom. Ar is an aryl group having a carbon number of from 5 to 12.

Especially preferred of these examples of the compound (51) and the compound (52) include the compounds shown below.

[Chem. 18]

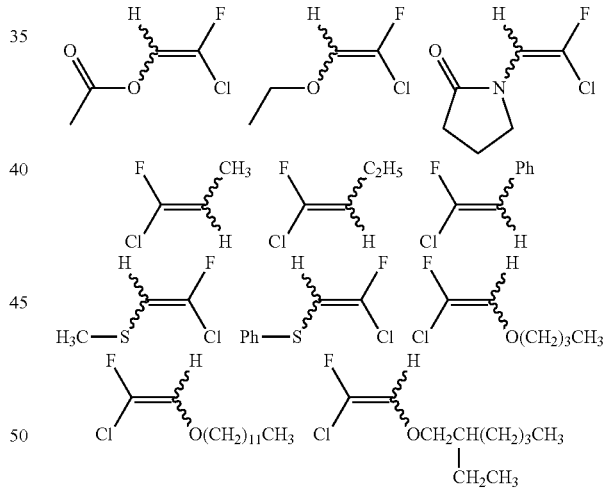

In the compound (51) and the compound (52), a chlorine atom is bonding to a carbon atom constituting the double bond. Because of this, it is easy to utilize these in a reaction in which the chlorine atom or the fluorine atom is selectively replaced (in particular, a reaction in which the chlorine atom is selectively replaced, while leaving the fluorine atom) or in a coupling reaction. Consequently, the compound (51) and the compound (52) to be obtained in the present invention are compounds useful as intermediates.

<Production Method>

The present invention relates to a production method for an olefin containing chlorine and fluorine through olefin metathesis, in which, typically, two different types of olefins are brought into contact with a metal-carbene complex to conduct olefin metathesis to give an olefin differing from the starting compounds.

Of the olefins as starting materials for use herein, the olefin that is not an olefin in which two fluorine atoms bond to one carbon atom constituting the double bond (the above-mentioned compound (31)) may be any of a terminal olefin or an internal olefin. The number of the substituents on the double bond is not specifically limited, but preferred are ethylene, monosubstituted olefins and 1,2-disubstituted olefins as having high reactivity. The geometric isomerism on the double bond is not also specifically limited. From the viewpoint of increasing the product yield, the olefins degassed and dried are preferably used as starting materials. The degassing operation is not specifically limited. Freeze-pump-thaw degasification or the like may be carried out. The drying operation is not also specifically limited. In general, it may be carried out by bringing into contact with a molecular sieve or the like. The degassing and drying operation for olefins as starting materials are generally conducted before they are brought into contact with the metal-carbene complex.

The olefins as starting materials may contain minor impurities (e.g., peroxides, etc.), and therefore may be purified from the standpoint of increasing the product yield. The purification method is not specifically limited. For example, it may be attained according to the methods described in literature [Armarego, W. L. F. et al., Purification of Laboratory Chemicals (Sixth Edition), 2009, Elsevier].

As the olefins where a chlorine atom and a fluorine atom bond to a carbon atom constituting the double bond [above-mentioned compound (21)] among the olefins containing chlorine and fluorine as starting materials, used are terminal olefins. That is, preferred examples thereof include R-1112, i.e., 1,2-dichloro-1,2-difluoroethylene, and R-1131a, i.e., 1-chloro-1-fluoroethylene and the like. From the viewpoint of increasing the product yield, the olefins containing chlorine and fluorine degassed and dried are preferably used as starting materials. The degassing operation is not specifically limited. Freeze-pump-thaw degasification or the like may be carried out. The drying operation is not also specifically limited. In general, it may be carried out by bringing into contact with a molecular sieve or the like. The degassing and drying operation for olefins containing chlorine and fluorine as starting materials are generally conducted before they are brought into contact with the metal-carbene complex.

The olefins containing chlorine and fluorine as starting materials may contain minor impurities (e.g., hydrogen fluoride, etc.), and therefore may be purified from the viewpoint of increasing the product yield. The purification method is not specifically limited. For example, it may be attained according to the methods described in literature [Armarego, W. L. F. et al., Purification of Laboratory Chemicals (Sixth Edition), 2009, Elsevier].

The olefins as starting materials (hereinafter the two types of olefins are collectively referred to as such) may be put into a reactor after they have been previously mixed, or may be put thereinto separately. With a mixture obtained by the contact of the first olefin with the metal-carbene complex may be brought into contact the second olefin.

The molar ratio of the both olefins as starting materials is not specifically limited. In general, based on one mol of one basis olefin, the other olefin is used in an amount of from 0.01 to 100 mol or so, and preferably from 0.1 to 10 mol or so.

The metal-carbene complex (the compound (11), compound (12), compound (13), compound (14), and compound (15)) may be put into as a reagent or may be generated in the system.

In the case where it is put into as a reagent, a commercially-available metal-carbene complex may be used directly as it is, or a commercially-unavailable metal-carbene complex synthesized from a commercially-available reagent according to a known method may be used.

In the case where it is generated in situ, a metal-carbene complex prepared from a metal complex as a precursor according to a known method may be used in the present invention.

The amount of the metal-carbene complex to be used is not particularly limited. It is used generally from 0.0001 to 1 mol or so, and preferably from 0.001 to 0.2 mol or so, based on one mol of one basis olefin of the olefins as starting materials.

The metal-carbene complex to be used is generally put into the reactor as it is solid, but may be put thereinto after dissolved or suspended in a solvent. The solvent to be used in the case is not specifically limited within a range not having any negative influence on the reaction. An organic solvent, a fluorine-containing organic solvent, an ionic liquid, water and the like may be used either singly or in combination thereof. Of these solvent molecules, a part or all of the hydrogen atoms may be substituted with deuterium atoms.

In the case where the compound (21) and/or the compound (31) is liquid (including the case where they liquefies upon heating), it is preferred not to use solvent. In this case, it is preferable that the metal catalyst dissolves in the compound (21) and/or the compound (31).

As the organic solvent, for example, usable are an aromatic hydrocarbon solvent such as benzene, toluene, o-, m- or p-xylene, mesitylene, or the like; an aliphatic hydrocarbon solvent such as hexane, cyclohexane or the like; a halogen-containing solvent such as dichloromethane, chloroform, 1,2-dichloroethane, chlorobenzene, o-dichlorobenzene, or the like; and an ether solvent such as tetrahydrofuran (THF), dioxane, diethyl ether, glyme, diglyme, or the like; and the like. As the fluorine-containing organic solvent, for example, usable are hexafluorobenzene, m-bis(trifluoromethyl)benzene, p-bis(trifluoromethyl)benzene, $\alpha,\alpha,\alpha$-trifluoromethylbenzene, dichloropentafluoropropane, and the like. As the ionic liquid, for example, usable are various pyridinium salts, various imidazolium salts, and the like. Of the above-mentioned solvents, benzene, toluene, o-, m- or p-xylene, mesitylene, dichloromethane, chloroform, chlorobenzene, o-dichlorobenzene, diethyl ether, dioxane, THF, hexafluorobenzene, m-bis(trifluoromethyl)benzene, p-bis(trifluoromethyl)benzene, $\alpha,\alpha,\alpha$-trifluoromethylbenzene, or the like, and mixtures thereof are preferred from the viewpoint of the solubility therein of the metal-carbene complex, or the like.

From the viewpoint of increasing the product yield, the solvent degassed and dried is preferably used. The degassing operation is not specifically limited. Freeze-pump-thaw degasification or the like may be carried out. The drying operation is not also specifically limited. In general, it may be brought into contact with a molecular sieve or the like. The degassing and drying operation is generally conducted before it is brought into contact with the metal-carbene complex The atmosphere in which the olefins are brought into contact with the metal-carbene complex is not particularly limited. From the viewpoint of prolonging a life of the catalyst, inert gas atmosphere is preferred, and above all, in particular, a nitrogen or argon atmosphere is preferred. However, in the case where an olefin which is gaseous under reaction conditions, such as, for example, R-1131a, i.e., 1-chloro-1-fluoroethylene or the like, are used as a starting material, the gaseous atmosphere of these can be employed.

The phase for contact between olefins and the metal-carbene complex is not particularly limited. From the viewpoint of reaction speed, a liquid phase is usually employed. In the case where the olefins as starting materials are gaseous under the reaction condition, the reaction is difficult to carry out in a liquid phase, and therefore may be carried out in a gaseous-liquid two-phase system. For the reaction in a liquid phase, a solvent may be used. As the solvent for use in the case, use can be made of the same as the solvent used for dissolving or suspending the metal-carbene complex. In the case where at least one of the olefins as starting materials is liquid under the reaction condition, the reaction may be carried out in the absence of a solvent.

The container in which olefins and the metal-carbene complex are brought into contact with each other is not specifically limited within a range not having any negative influence on the reaction. For example, metal containers, glass containers and the like are usable. In olefin metathesis according to the present invention, olefins that are gaseous under the reaction condition may be processed, and therefore preferred are airtightly-closable pressure-proof containers.

The temperature at which olefins and the metal-carbene complex are brought into contact with each other is not specifically limited. In general, it may be carried out in a range of from −100 to 200° C., and from the viewpoint of the reaction speed, it is preferably from 0 to 150° C. As the case may be, the reaction could not start at low temperatures, and the complex would rapidly decompose at high temperatures, and consequently, the lower limit and the upper limit of the temperature range must be defined case by case. In general, the reaction may be carried out at a temperature not higher than the boiling point of the solvent used.

The time for which olefins and the metal-carbene complex are brought into contact with each other is not specifically limited. In general, the reaction is carried out in a range of from 1 minute to 48 hours.

The pressure under which olefins and the metal-carbene complex are brought into contact with each other is not specifically limited. The reaction may be carried out under elevated pressure, under normal pressure or under reduced pressure. In general, it is from 0.001 to 10 MPa or so, and preferably from 0.01 to 1 MPa or so.

In the contact of olefins with the metal-carbene complex, an inorganic salt, an organic compound, a metal complex or the like may be made to exist in the system within a range not having any negative influence on the reaction. Also within a range not having any negative influence on the reaction, the mixture of olefins and the metal-carbene complex may be stirred. In stirring method in this case, usable is a mechanical stirrer, a magnetic stirrer or the like.

After olefins and the metal-carbene complex have been brought into contact with each other, an intended object may be obtained generally as a mixture of plural olefins. Therefore, it may be isolated according to a known method. Examples of the isolation method include distillation, column chromatography, recycling preparative HPLC, and the like. If desired, these may be employed either singly or in combination of plural kinds thereof.

The intended object obtained in this reaction may be identified according to known methods that are the same as the method for ordinary organic compounds. For example, there are mentioned $^1$H-, $^{19}$F-, or $^{13}$C-NMR, GC-MS, and the like. If desired, these may be employed either singly or in combination of plural kinds thereof.

The present invention is explained below in detail with reference to Examples, but the present invention is not limited to these.

<Commercial Reagents>

In the Examples, as for the catalyst, commercial products were used in the reaction directly as they are, unless otherwise specifically indicated. As for the solvents (benzene-$d_6$ and o-dichlorobenzene-$d_4$) and an the internal standard [p-bis(trifluoromethyl)benzene], commercial products were previously degassed by freeze-pump-thaw cycles, then dried over Molecular Sieve 4A, and used in the reaction.

<Evaluation Method>

The structure of the compound synthesized in the Examples was identified through measurement of $^1$H-NMR and $^{19}$F-NMR spectroscopy using a nuclear magnetic resonance apparatus (JNM-AL300) manufactured by JEOL Ltd. The molecular weight was measured according to an electron ionization method (EI) using a gas chromatography mass spectrometer (GCMS-QP2010Ultra) manufactured by Shimadzu.

EXAMPLE 1

Metathesis of Dodecyl Vinyl Ether and 1,2-dichloro-1,2-difluoroethylene (R-1112) with Umicore M73SIPr Catalyst In a nitrogen atmosphere, dodecyl vinyl ether (0.06 mmol), Umicore M73SIPr catalyst (10 mol %; 0.006 mmol), 1,2-dichloro-1,2-difluoroethylene (R-1112) (0.06 mmol), and m-xylene-$d_{10}$ (0.6 mL) containing p-bis(trifluoromethyl)benzene (internal standard; 0.02 mmol) dissolved therein were weighed and put into an NMR tube.

The NMR tube was heated at 60° C., and the reaction was conducted at that temperature for 1 hour. After completion of the reaction, NMR and GC-MS of the liquid content were measured to confirm the formation of (2-chloro-2-fluorovinyl) dodecyl ether.

The series of the reaction is shown below. The catalyst turnover number (catalyst turnover frequency per hour) calculated from the $^{19}$F-NMR spectrum [internal standard, p-bis(trifluoromethyl)benzene] was 0.5.

[Chem. 19]

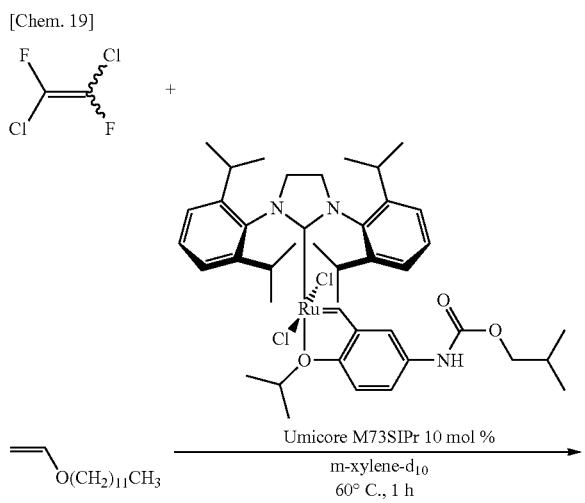

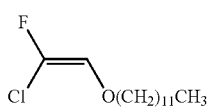

REFERENCE EXAMPLE 1

Metathesis of Dodecyl Vinyl Ether and 1,2-dichloro-1,2-difluoroethylene (R-1112) with Commercial Molybdenum Catalyst B In a nitrogen atmosphere, a commercial molybdenum catalyst B (2 mol %; 0.0012 mmol), dodecyl vinyl ether (0.06 mmol), 1,2-dichloro-1,2-difluoroethylene (R-1112) (0.12 mmol), and benzene-$d_6$ (0.6 mL) containing p-bis(trifluoromethyl)benzene (internal standard; 0.01 mmol) dissolved therein were weighed and put into a pressure-proof NMR tube.

The NMR tube was heated at 60° C. and held at that temperature for 1 hour. After the 1-hour holding, the starting materials only were recovered and the desired product was not obtained.

[Chem. 20]

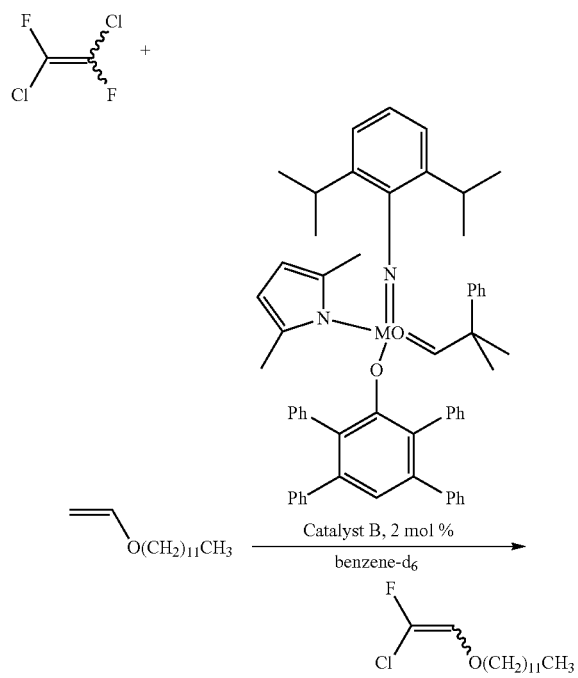

REFERENCE EXAMPLE 2

Metathesis of Dodecyl Vinyl Ether and 1,2-dichloro-1,2-difluoroethylene (R-1112) with Commercial Molybdenum Catalyst C In a nitrogen atmosphere, a commercial molybdenum catalyst C (2 mol %; 0.0012 mmol), dodecyl vinyl ether (0.06 mmol), 1,2-dichloro-1,2-difluoroethylene (R-1112) (0.12 mmol), and benzene-$d_6$ (0.6 mL) containing p-bis(trifluoromethyl)benzene (internal standard; 0.01 mmol) dissolved therein were weighed and put into a pressure-proof NMR tube.

The NMR tube was heated at 60° C. and held at that temperature for 1 hour. After the 1-hour holding, the starting materials only were recovered and the desired product was not obtained.

[Chem. 21]

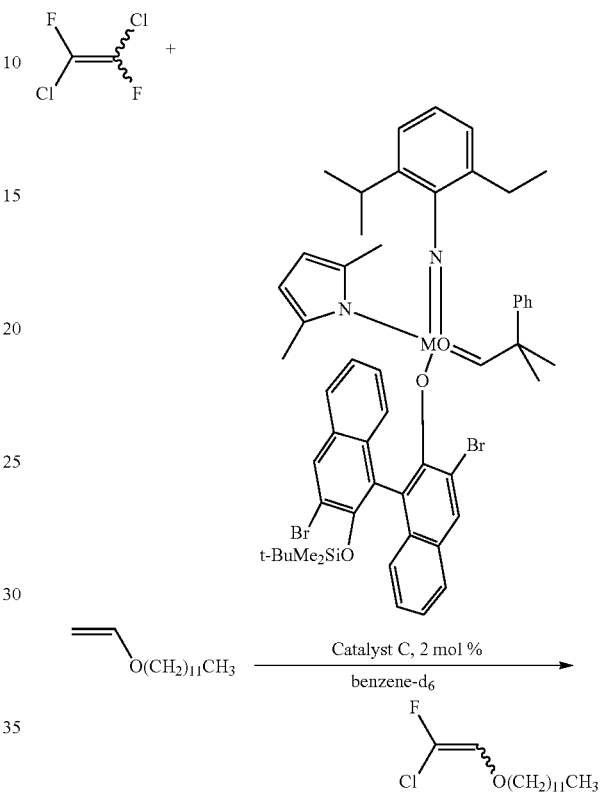

EXAMPLE 2

Metathesis of Butyl Vinyl Ether and 1,2-dichloro-1,2-difluoroethylene (R-1112) with Commercial Molybdenum Catalyst D In a nitrogen atmosphere, a commercial molybdenum catalyst D (2 mol %; 0.0012 mmol), butyl vinyl ether (0.06 mmol; previously degassed by freeze-pump-thaw cycles and dried over potassium hydroxide), 1,2-dichloro-1,2-difluoroethylene (R-1112) (0.12 mmol), and benzene-$d_6$ (0.6 mL) containing p-bis(trifluoromethyl)benzene (internal standard; 0.02 mmol) dissolved therein are weighed and put into a pressure-proof NMR tube.

The NMR tube is heated at 60° C. and the reaction is conducted at that temperature for 1 hour. After completion of the reaction, NMR and GC-MS of the liquid content are measured to confirm the formation of butyl (2-chloro-2-fluorovinyl) ether.

[Chem. 22]

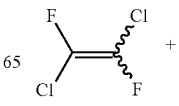

-continued

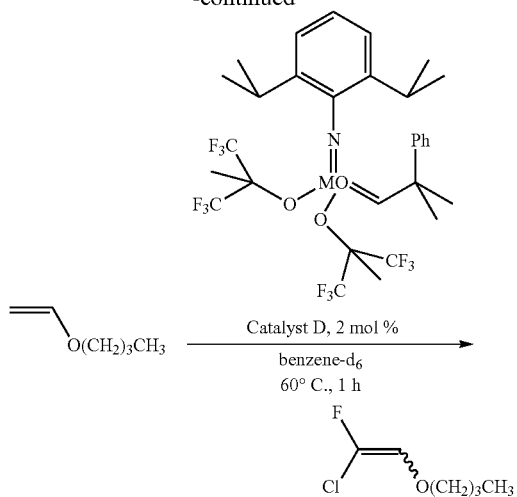

EXAMPLES 3 AND 4

The 1,2-dichloro-1,2-difluoroethylene in Example 1 is replaced with each of the compounds shown in Table 1, and the reaction is conducted. The compounds shown in Table 1 are produced as products.

TABLE 1

| Example | Compound (21) | Product Compound (51) and Compound (52) |
|---|---|---|
| 3 | F₂C=CHCl | F(Cl)C=CH–O(CH₂)₃CH₃ |
| 4 | Cl₂FC–CF=CFCl | F₂C=CFCl + F(Cl)C=CF–O(CH₂)₃CH₃ |

EXAMPLES 5 AND 6

The 1,2-dichloro-1,2-difluoroethylene in Example 2 is replaced with each of the compounds shown in Table 2, and the reaction is conducted. The compounds shown in Table 2 are produced as products.

TABLE 2

| Example | Compound (21) | Product Compound (51) and Compound (52) |
|---|---|---|
| 5 | F₂C=CHCl | F(Cl)C=CH–O(CH₂)₃CH₃ |
| 6 | Cl₂FC–CF=CFCl | F₂C=CFCl + F(Cl)C=CF–O(CH₂)₃CH₃ |

EXAMPLES 7 AND 8

The butyl vinyl ether in Example 1 is replaced with each of the compounds shown in Table 3, and the reaction is conducted. The compounds shown in Table 3 are produced as products.

TABLE 3

| Example | Compound (31) | Product Compound (51) and Compound (52) |
|---|---|---|
| 7 | CH₃C(O)O–CH=CH₂ | F₂C=CFCl + F(Cl)C=CH–OC(O)CH₃ |
| 8 | N-vinyl-2-pyrrolidone | F₂C=CFCl + F(Cl)C=CH–N(pyrrolidinone) |

EXAMPLE 9

Metathesis of Butyl Vinyl Ether and Tetrafluoroethylene with Commercial Molybdenum Catalyst D In a nitrogen atmosphere, the commercial molybdenum catalyst D (1 mol %), 1,2-dichloro-1,2-difluoroethylene (R-1112) (0.12 mmol), and butyl vinyl ether (0.12 mmol; previously degassed by freeze-pump-thaw cycles and dried over potassium hydroxide) are weighed and put into a pressure-proof reactor.

The NMR tube is heated at 60° C., and the reaction is conducted at that temperature for 1 hour. After completion of the reaction, NMR and GC-MS of the liquid content are measured to confirm the formation of butyl (2-chloro-2-fluorovinyl) ether.

The series of the reaction is shown below.

[Chem. 23]

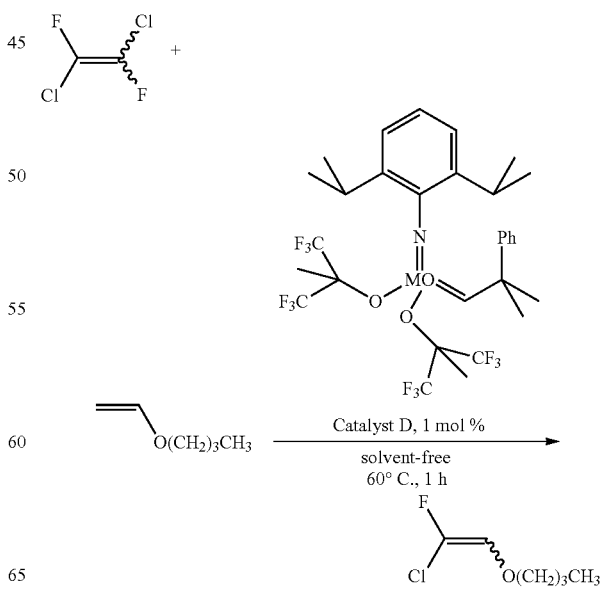

INDUSTRIAL APPLICABILITY

According to the present invention, other olefins containing chlorine and fluorine can be simply and efficiently produced from industrially-easily-available olefins containing chlorine and fluorine such as R-1112, i.e., 1,2-dichloro-1,2-difluoroethylene, or R-1131a, i.e., 1-chloro-1-fluoroethylene through olefin metathesis.

While the present invention has been described in detail and with reference to specific embodiments thereof, it will be apparent to one skilled in the art that various changes and modifications can be made therein without departing from the spirit and scope thereof. This application is based on a Japanese patent application filed on Dec. 26, 2014 (Application No. 2014-266097), the contents thereof being incorporated herein by reference.

The invention claimed is:

1. A method for producing at least one olefin compound selected from the group consisting of a compound of formula (51) and a compound of formula (52), the method comprising:

reacting an olefin compound of formula (21) with a olefin compound of formula (31) in the presence of at least one metal catalyst selected from the group consisting of a compound of formula (11), a compound of formula (12), a compound of formula (13), a compound of formula (14), and a compound of formula (15):

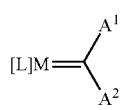
(11)

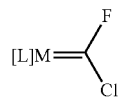
(12)

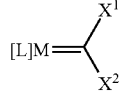
(13)

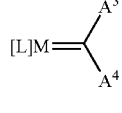
(14)

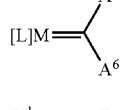
(15)

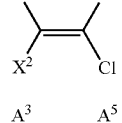
(21)

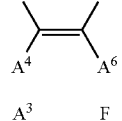
(31)

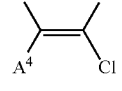
(51)

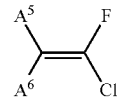
(52)

wherein [L] is a ligand;

M is molybdenum or tungsten and the metal catalyst has an imide ligand and a ligand including two coordinating oxygen atoms as the ligand [L];

$A^1$ to $A^6$ are each independently a functional group selected from the group consisting of functional group (i), functional group (ii), functional group (iii), and functional group (iv);

$A^1$ and $A^2$ may bond to each other to form a ring;
$A^3$ and $A^4$ may bond to each other to form a ring;
$A^5$ and $A^6$ may bond to each other to form a ring;

provided that in the case where one of $A^1$ or $A^2$ is a halogen atom, the other is a functional group selected from the group consisting of the functional group (i), the functional group (iii) and the functional group (iv);

in the case where one of $A^3$ or $A^4$ is a halogen atom, the other is a functional group selected from the group consisting of the functional group (i), the functional group (iii) and the functional group (iv); and in the case where one of the $A^5$ or $A^6$ is a halogen atom, the other is a functional group selected from the group consisting of the functional group (i), the functional group (iii) and the functional group (iv); and $X^1$ is a fluorine atom, and $X^2$ is independently a functional group selected from the group consisting of the functional group (i), the functional group (ii), the functional group (v), and the functional group (vi);

provided that in the case where one of $X^1$ or $X^2$ is a fluorine atom, the other is a functional group selected from the group consisting of the functional group (i), a halogen atom except for a fluorine atom, the functional group (v) and the functional group (vi):

functional group (i): a hydrogen atom;
functional group (ii): a halogen atom;
functional group (iii): a monovalent hydrocarbon group having a carbon number of from 1 to 20;
functional group (iv): a monovalent hydrocarbon group having a carbon number of from 1 to 20 and containing one or more atoms selected from the group consisting of a halogen atom, an oxygen atom, a nitrogen atom, a sulfur atom, a phosphorus atom, and a silicon atom;
functional group (v): a functional group selected from the group consisting of an alkyl group having a carbon number of from 1 to 12, an alkoxy group having a carbon number of from 1 to 12, an acyl group having a carbon number of from 5 to 20, an aryloxy group having a carbon number of from 5 to 20, a (per)halogenated alkyl group having a carbon number of from 1 to 12, a (per)halogenated alkoxy group having a carbon number of from 1 to 12, a (per)halogenated aryl group having a carbon n her of from 5 to 20, and a (per)halogenated aryloxy group having a carbon number of from 5 to 20; and
functional group (vi): the functional group (v) containing one or more atoms selected from the group consisting of an oxygen atom, a nitrogen atom, a sulfur atom, a phosphorus atom, and a silicon atom.

2. The production method according to claim 1, comprising reacting at least one compound selected from the group consisting of 1,2-dichloro-1,2-difluoroethylene, and 1,3,3-trichloro-1,2,3-trifluoropropene with the olefin compound of formula (31).

3. The production method according to claim 1, wherein the olefin compound of formula (31) is ethylene, a monosubstituted olefin, or a 1,2-disubstituted olefin.

4. The production method according to claim 1, wherein in the olefin compound of formula (31), $A^3$ is a hydrogen atom and $A^4$ is a hydrogen atom, a monovalent hydrocarbon group having a carbon number of from 1 to 20, or a monovalent hydrocarbon group having a carbon number of from 1 to 20 and containing one or more atoms selected from the group consisting of a halogen atom, an oxygen atom, a nitrogen atom, a sulfur atom, a phosphorus atom, and a silicon atom.

5. The production method according to claim 1, wherein the olefin compound of formula (31) is at least one olefin compound selected from olefin compounds represented by the following formulae:

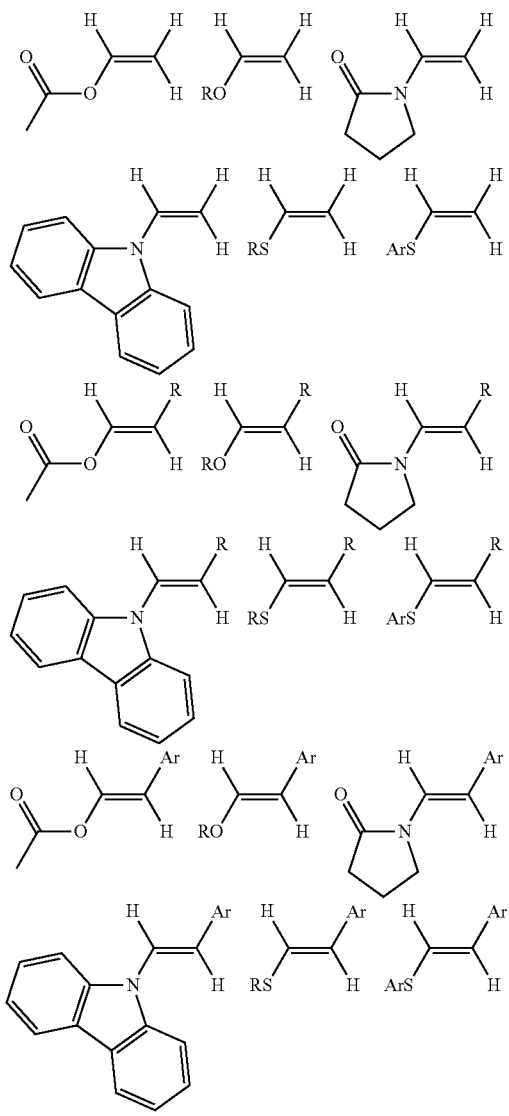

wherein R is an alkyl group having a carbon number of from 1 to 12 or an alkyl group having a carbon number of from 1 to 12 and having an etheric oxygen atom between a carbon atom and a carbon atom, and Ar is an aryl group having a carbon number of from 5 to 12.

6. The production method according to claim 1, wherein the olefin compound of formula (31) is an olefin compound having a heteroatom existing adjacent to a carbon atom of the olefin.

7. The production method according to claim 6, wherein the heteroatom is an oxygen atom or a nitrogen atom.

8. The production method according to claim 1, wherein the reacting forms at least one olefin compound selected from olefin compounds represented by the following formulae as the compound of formula (51) and the compound of formula (52):

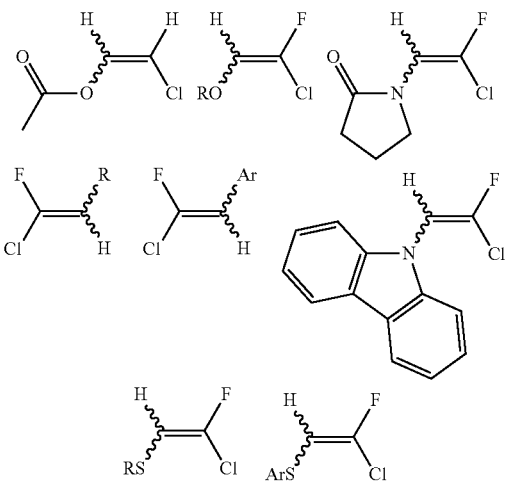

wherein R is an alkyl group having a carbon number of from 1 to 12 or an alkyl group having a carbon number of from 1 to 12 and having an etheric oxygen atom between a carbon atom and a carbon atom, and Ar is an aryl group having a carbon number of from 5 to 12.

9. The production method according to claim 1, wherein a temperature during the reacting is from 0 to 150° C.

10. The production method according to claim 1, wherein the reacting is carried out in the absence of a solvent.

11. The production method according to claim 1, wherein the compound of formula (31) is an alkyl vinyl ether.

12. The production method according to claim 1, wherein the compound of formula (31) is at least one selected from the group consisting of dodecyl vinyl ether and butyl vinyl ether.

13. The production method according to claim 1, wherein the compound of formula (31) is selected from the group consisting

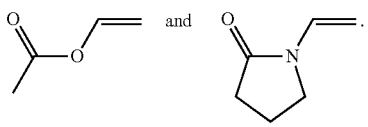

14. The method according to claim 1, wherein the compound of formula (21) is 1,2-dichloro-1,2-difluoroethylene.

15. The production method according to claim 1, wherein the metal catalyst is

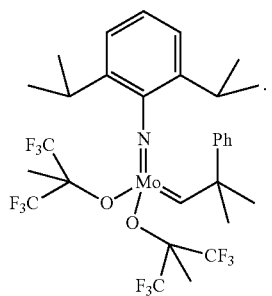
* * * * *